US 7,122,526 B2

(12) United States Patent
Xu et al.

(10) Patent No.: US 7,122,526 B2
(45) Date of Patent: *Oct. 17, 2006

(54) INDOLOCARBAZOLE ANTICANCER AGENTS AND METHODS OF USING SAME

(75) Inventors: Ze-Qi Xu, Woodridge, IL (US);
Yasheen Zhou, Moraga, CA (US);
Michael T. Flavin, Darien, IL (US)

(73) Assignee: Nanosphere, Inc., Northbrook, IL (US)

( * ) Notice: Subject to any disclaimer, the term of this patent is extended or adjusted under 35 U.S.C. 154(b) by 367 days.

This patent is subject to a terminal disclaimer.

(21) Appl. No.: 10/610,290

(22) Filed: Jun. 30, 2003

(65) Prior Publication Data

US 2004/0077554 A1   Apr. 22, 2004

Related U.S. Application Data

(63) Continuation-in-part of application No. 10/057,260, filed on Oct. 29, 2001, now Pat. No. 6,605,596.

(60) Provisional application No. 60/244,469, filed on Oct. 31, 2000.

(51) Int. Cl.
| A01N 43/04 | (2006.01) |
| A61K 31/70 | (2006.01) |
| C07G 3/00 | (2006.01) |
| C07G 11/00 | (2006.01) |
| C07H 15/00 | (2006.01) |
| C07H 17/00 | (2006.01) |

(52) U.S. Cl. .......................... 514/43; 514/25; 536/17.4; 536/17.7; 536/18.7

(58) Field of Classification Search ............. 536/17.4, 536/17.7, 18.7; 514/25, 43
See application file for complete search history.

(56) References Cited

U.S. PATENT DOCUMENTS

| 5,106,742 A | 4/1992 | Wall et al. |
| 5,401,747 A | 3/1995 | Wall et al. |
| 5,437,996 A | 8/1995 | Kojiri et al. |
| 5,559,235 A | 9/1996 | Luzzio et al. |
| 5,589,365 A | 12/1996 | Kojiri et al. |
| 5,591,842 A | 1/1997 | Kojiri et al. |
| 5,643,760 A | 7/1997 | Kojiri et al. |
| 5,668,271 A | 9/1997 | Kojiri et al. |
| 5,804,564 A | 9/1998 | Kojiri et al. |
| 5,859,261 A | 1/1999 | Faul et al. |
| 5,883,114 A | 3/1999 | Kleinschroth et al. |
| 5,922,860 A | 7/1999 | Kojiri et al. |

FOREIGN PATENT DOCUMENTS

| WO | WO 96/04293 | 2/1996 |
| WO | WO 97/09339 | 3/1997 |

OTHER PUBLICATIONS

Anizon, et al., "Syntheses and Biological Activities (Topoisomerase Inhibition and Antitumor and Antimicrobial Properties) of Rebeccamycin Analogues Bearing Modified Sugar Moieties and Substituted on the Imide Nitrogen with a Methyl Group," *J. Med. Chem*, vol. 40, 1997, pp. 3456-3465.

Pereira, et al., "Structure-Activity Relationship in a Series of Substituted Indolocarbazoles: Topoisomerase I and Protein Kinase C inhibition and Antitumoral and Antimicrobial Properties," *J. Med. Chem*. vol. 39, 1996, pp. 4471-4477.

Yamashita, et al., "Induction of Mammalian DNA Topoisomerase I Mediated DNA Cleavage by Antitumor Indolocarbazole Derivatives," *Biochemistry* 1992, vol. 31, pp. 12069-12075.

Zembower, et al., "Indolocarbazole Poisons of Human Topoisomerase I: Regioisomeric Analogues of ED-110" *Bioorganic & Medicinal Chemistry Letters 9*, 1999, pp.145-150.

(Continued)

*Primary Examiner*—Patrick Lewis
(74) *Attorney, Agent, or Firm*—McDonnell Boehnen Hulbert & Berghoff LLP

(57) ABSTRACT

The present invention relates to anti-tumor compounds, compositions and methods. In particular, the invention relates to indolocarbazole analogues of the following general formulas that inhibit topoisomerase I activity 16 Claims, No Drawings

OTHER PUBLICATIONS

Arakawa, et al, "Novel Indolocarbazole Compound 6-N-Formylamino-12, 13-dihydro-1,11-dihydroxy-13-(β-D-glucopyranosyl)-5-H-indolo[2,3-a]pyrrolo-[3,4-c] carbazole-5,7 (6H)-dione (NB-506): It's Potent Antitumor Activities in Mice", *Cancer Research.*, vol. 55, p. 1316-1320, 1995.

Arakawa, et al., "ED-110, a Novel Indolcarbazole, Prevents the Growth of Experimental Tumors in Mice", *Japan. Journal Cancer Res.*, 84, p. 574-581, May 1993.

Batcho et al., "Indoles from 2-Methylinitorbenzenes by Condensation with formamide Acetals Followed by Reduction: 4-Benzyloxyindole", *Organic Syntheses. Collective Volumes III*, p. 34-41, 1990.

Champoux, "Mechanism of Catalysis by Eukaryotic DNA Topoisomerase I", *Adv. Pharmacol.*, 29A, p. 71-82, 1994.

Kaneko, et al., "Two Synthetic Approaches to Rebeccamycin", *Tetrahedron Letters*, vol. 16, No. 34, p. 4015-4018, 1985.

Ohkubo, et al., "Synthesis of Dissymmetric Indolocarbazole Glycosides Using the Mitsunobu Reaction at the Glycosylation Step", *Tetrahedron*, vol. 53, No. 17, p. 5937-5950, 1997.

Pommier, et al., "Mechanisms of Topoisomerase I Inhibition by Anticancer Drugs", *Advances in Pharmacology*, vol. 29B, p. 73-92, 1994.

Redinbo, et al., "Crystal Structures of Human Topoisomerase I in Covalent and Noncovalent Complexes with DNA", *Science*, vol. 279, p. 1504-1513, 1998.

Yoshinari, et al., "Mode of Action of a New Indolocarbazole Anticancer Agent, J-107088, Targeting Topoisomerase I" *Cancer Research*, vol. 59, p. 4271-4275, 1999.

Bailley et al., "DNA Cleavage by Topoisomerase I in the Presence of Indolocarbazole Derivatives of Rebeccamycin," *Biochemistry*, vol. 36, 1997, pp. 3917-3929.

Bailley et al., "Enhanced Binding to DNA and Topoisomerase I Inhibition by an Analog of the Antitumor Antibiotic Rebecamycin Containing an Amino Sugar Residue," *Molecular Pharmacology*, vol. 55, 1999, pp. 377-385.

Labourier et al., "Poisoning of Topoisomerase I by an Antitumor Indolocarbazole Drug: Stabilization of Topoisomerase I-DNA Covalent Complexes and Specific Inhibition of the Protein Kinase Activity," *Cancer Research*, vol. 59, 1999, pp. 52-55.

Okhubo et al., "Synthesis and Biological Activities of NB-506 Analogues: Effects of the Positions of two Hydroxyl Groups at the Indole Rings," *Bioorganic & Medicinal Chemistry Letters*, vol. 9, 1999, pp. 3307-3312.

Okhubo et al., "Synthesis and Biological Activities of NB-506 Analogues Modified at the Glucose Group," *Bioorganic & Medicinal Chemistry Letters*, vol. 10, 2000, pp. 419-422.

Anizon et al., "Syntheses and Biological Activities (Topoisomerase Inhibition and Antitumor and Antimicrobial Properties) of Rebeccamycin Analogues Bearing Modified Sugar Moieties and Substituted on the Imide Nitrogen with a Methyl Group", *J. Med. Chem.*, 1997, vol. 40, p. 3456-3465.

Bailly et al., "DNA Cleavage by Topoisomerase I in the Presence of Indolocarbazole Derivatives of Rebeccamycin", *Biochemsitry*, 1997, vol. 36, p. 3917-3929.

Bailly et al., "Enhanced Binding to DNA and Topoisomerase I Inhibition by an Analog of the Antitumor Antibiotic Rebeccamycin Containing an Amino Sugar Residue", *Molecular Pharmacology*, 1999, vol. 55, p. 377-385.

Labourier et al., "Poisoning of Topoisomerase I by an Antitumor Indolocarbazole Drug: Stabilization of Topoisomerase I-DNA Covalent Complexes and Specific Inhibition of the Protein Kinase Activity", *Cancer Research*, Jan. 1, 1999, vol. 59, p. 52-55.

Okhubo et al., "Synthesis and Biological Activities of NB-506 Analogues Modified at the Glucose Group," *Bioorganic & Medicinal Chemistry Letters*, 2000, vol. 10, pp. 419-422.

Glosssary Entry for Anomer, p. 1 of 1[online], [retrieved on Feb. 6. 2002]. Retrieved from Internet: <URL: http://www.vel.co.uk/TGN/glossary/entries/anomer.html>.

Molecular Recognition of Carbohydrates, pp. 1-6 [online], [retrieved on Feb. 6, 2002]. Retrieved from the Internet: <URL: http://www.nmr.chem.uu.n1/~abonvin/ToT/damm/index.html>.

Monosaccharides Form Rings, pp. 1-2, Cabrillo College Chem 12B, Spring 1998 [online]. [retrieved on Apr. 1, 1999]. Retrieved from the Internet: <URL: http://www.cabrillo.cc.ca.us./divisions/becho/chem/hungar/exercise_3/html/12b33.html>.

Nomenclature of Carbohydrates (Recommendations 1996) 2-Carb-33, pp. 1-9 [online], [retrieved on Apr. 2, 1999]. Retrieved from the Internet: <URL: http://www.chem.qmw.ac.uk/lupac/2carb/33.html>.

Prevention of Anomer Separation, Monosaccharides and oligosaccarides, p. 1 [online], [retrieved on Apr. 1, 1999]. Retrieved from the Internet: <URL: http://www.hplc1.com/shodez/english/dc030202.htm>.

Sci.chem FAQ—Part 7 of 7 [online], [retrieved on Feb. 6, 2002]. Retrieved from the Internet: <URL: http:www.faqs.org/faqs/sci/chem-faq/part7/preamble.html>.

Stereo Oligomers and Polymers from Glycals: Oligomerisations, pp. 1-2 [online], [retrieved on Feb. 6, 2002]. Retrieved from the Internet: <URL: http://www.ch.ic.ac.uk./ectoc/echet96/papers/008/oligomers.html>.

Stereochemistry of Glycosyl Transfer: Interaction with "glucose" Active site of the Enzyme, pp. 1-2 [online], [retrieved on Feb. 6, 2002]. Retrieved from the Internet: <URL: http://www.netsci-journal.com/97v1/97005/005p30.htm>.

INDOLOCARBAZOLE ANTICANCER AGENTS AND METHODS OF USING SAME

RELATED APPLICATIONS

This application is a continuation-in-part of U.S. patent application Ser. No. 10/057,260, filed Oct. 29, 2001 now U.S. Pat. No. 6,605,596 which claims the benefit of priority from U.S. provisional application No. 60/244,469, filed Oct. 31, 2000, the contents of which are incorporated herein by reference in their entirety.

FIELD OF THE INVENTION

This invention relates to synthetic indolocarbazole analogues and uses thereof. More particularly, this invention relates to compounds having modifications of the core structure 12-(β-D-glucopyranosyl)-6,7,12,13-tetrahydroindolo[2,3-a]pyrrolo[3,4-c]carbazole-5,7-dione, containing substitutions consisting of a 2,3,9-trihydroxy pattern, particularly cyclic and acyclic ethers at the 2- and 3-hydroxy positions. The present invention further relates to compounds having modifications of the indolocarbazole core structure by introducing an additional ring structure. The present invention also relates to compositions and methods of using such indolocarbazole analogues for the inhibition of topoisomerase I activity, which are useful in inhibiting the proliferation of tumor cells.

BACKGROUND OF THE INVENTION

Human topoisomerase I (Topo I) is an enzyme critical to the viability of cellular function that is an attractive target for the design and development of anticancer therapeutics. Currently there are two anticancer agents approved by the Food and Drug Administration for the clinical treatment of cancers: topotecan (Hycamtin) and CPT-11 (Camptosar), both of which are structural analogues of the natural product camptothecin.

Eukaryotic DNA Topoisomerase I (Topo I) is an essential nuclear enzyme responsible for the organization and modulation of the topological dilemmas in DNA, such as overwinding, underwinding and catenation. Topo I plays a critical role in allowing a cell to appropriately replicate, transcribe, repair genetic information, and perhaps carry out other DNA processes such as chromatin assembly, recombination and chromosome segregation.[1,2]

Topo I is a 100 kD monomeric protein that catalyzes changes in the topological state of double-stranded DNA (dsDNA) in increments of one linking number.[3] The three-dimensional structure of human Topo I has been reported.[4] The mechanism by which Topo I acts is believed to proceed through induction of a transient single-stranded break in dsDNA via formation of a covalent protein-DNA adduct referred to as the cleavable complex, so named because these complexes are detected as DNA breaks upon treatment with denaturing agents or alkali. The cleavable complex is formed upon transesterification of a DNA phosphodiester linkage by the active site tyrosine-723 residue on human Topo I, resulting in an ester linkage between the enzyme and the 3'-phosphoryl end of the broken DNA strand. This allows free rotation of the protein-bound 3' end of the broken DNA strand about the intact complementary DNA strand, resulting in relaxation of the duplex in increments of one linking number. Religation of the broken strand (via a second transesterification reaction) and subsequent dissociation of topoisomerase I completes the catalytic cycle.

Topoisomerase I poisons act via stabilization of the cleavable complex, mediated by formation of a ternary complex consisting of drug, topoisomerase I and DNA.[5] Agents such as camptothecin (the prototype topoisomerase I poison) do not bind to DNA directly, nor to topoisomerase I alone, but only to topoisomerase I complexed with DNA. It has been postulated that the stabilized DNA-protein-drug complex causes lethal DNA strand breaks upon collision with the advancing replication fork. It is by this mechanism that the topoisomerase I poison converts the enzyme into a DNA damaging agent, resulting in disruption of DNA replication and, eventually, cell death. This postulate is supported by the fact that camptothecin is highly phase-specific, only killing cells in S-phase.

It has been reported that intracellular levels of topo I are elevated in a number of human solid tumors, relative to the respective normal tissues, suggesting that variations in topo I levels are tumor type specific.[6-8] Thus, topo I represents a promising target for the development of new cancer chemotherapeutic agents against a number of solid tumors. Development of anti-topo I agents offers a new approach to the multi-regimental arsenal of therapies currently used in the clinic for the treatment of cancer.

In addition to the camptothecins, indolocarbazoles have also demonstrated potent antitumor activity via the poisoning of topoisomerase I activity,[9-12] most notably ED-110,[13] NB-506,[14] and J-107088.[15] The indolocarbazole analogue bearing a 3,9-dihydroxy substitution pattern was found to have superior topoisomerase I poisoning capability as well as superior in vitro antitumor activity relative to the other "symmetrical" dihydroxylated regioisomers.[16] The 3,9-dihydroxy analogue also exhibited impressive in vivo antitumor activity against the DU-145 human prostate tumor line xenotransplanted into nude mice.

SUMMARY OF THE INVENTION

The present invention relates to compounds, compositions and methods for the inhibition of topoisomerase I activity.

Accordingly, one object of the invention is to provide compounds of the general formulas I and II,

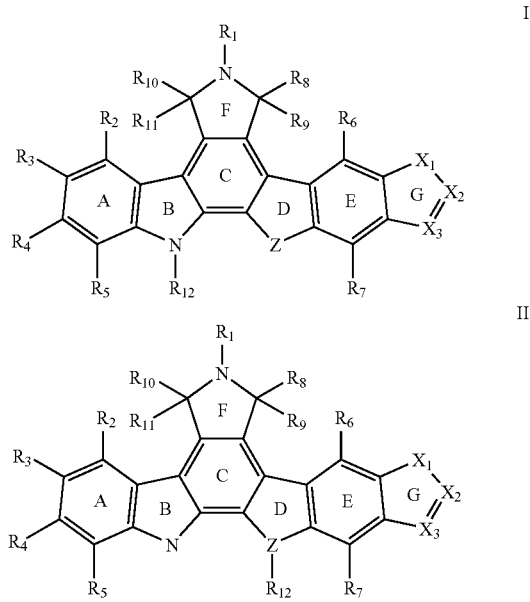

$R_1$ is selected from the group consisting of H, OH, $NH_2$, $NO_2$, $SO_2NRR'$, COR, $CO_2R$ and CONRR', alkylcarbonyl, alkylcarbonyloxy, $C_{1-6}$ alkyl, $C_{1-6}$ alkyloxy, $C_{1-6}$ alkylamino, di($C_{1-6}$ alkyl)amino, $C_{1-6}$ alkylamino-$C_{1-6}$ alkyl, di($C_{1-6}$ alkyl)amino-$C_{1-6}$ alkyl, or cyclo($C_{3-6}$)alkyl, $C_{1-6}$ alkylsulphinyl, $C_{1-6}$ alkylsulphonyl, wherein said alkyl is straight-chained or branched, saturated or unsaturated, and is optionally substituted with one or more substituents selected from the group consisting of halogen, $N_3$, CN, $NO_2$, SR, OR, NRR', SOR, $SO_2R$, $SO_3R$, $SO_2NRR'$, COR, $CO_2R$ and CONRR', or aryl, aryl-$C_{1-6}$ alkyl, aryloxy, aryl-$C_{1-6}$ alkyloxy, arylcarbonyloxy, arylamino, di(aryl)amino, aryl-$C_{1-6}$ alkylamino, di(aryl-$C_{1-6}$ alkyl)amino, arylsulphinyl, arylsulphonyl, wherein said alkyl is defined as above; aryl comprises six membered aromatic carbocycles such as phenyl or a polycyclic aromatic hydrocarbon such as naphthyl, phenanthracenyl, indanyl, indenyl, and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or heterocycle, (heterocycle)$C_{1-6}$ alkyl, (heterocycle)oxy, (heterocycle)-$C_{1-6}$ alkyloxy, (heterocycle)carbonyloxy, (heterocycle)amino, di(heterocycle)amino, [(heterocycle) $C_{1-6}$ alkyl]amino, di[(heterocycle)$C_{1-6}$ alkyl]amino, wherein said alkyl is defined as above; heterocycle comprises 3–8 membered heterocycles such as oxirane, aziridine, pyrrole, pyrroline, pyrrolidine, pyrrolidone, pyrrolindione, pyrazole, imidazole, imidazoline, triazole, (1,2,4)-triazine-3,5-dione, furan, tetrahydrofuran, thiophene, oxazole, thiazole, pyridine, pyrimidine, pyridazine, pyrazine, piperidine, piperazine, pyran, morpholine, azepine, or polycyclic systems such as indole, indoline, indolizine, isoindole, indazole, benzthiophene, isobenzthiophene, benzofuran, isobenzofuran, benzimidazole, benzoxazole, benzothiazole, benzotriazole, quinoline, isoquinoline, quinazoline, benzotriazine, flavone, phenanthridine, and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbocycle, carbocycle-$C_{1-6}$ alkyl, (carbocycle)oxy, (carbocycle)$C_{1-6}$ alkyloxy, (carbocycle)carbonyloxy, (carbocycle)amino, di(carbocycle)amino, [(carbocycle)$C_{1-6}$ alkyl]amino, di[(carbocycle) $C_{1-6}$ alkyl]amino, wherein said alkyl is defined as above; carbocycle comprises 3–8 membered carbocycles such as cyclopropane, cyclobutane, cyclobutene, cyclopentane, cyclopentene, cyclopentadiene, cyclohexane, cycloheptane, cyclooctane, or polycyclic systems such as bicycle[1.1.0]butane, bicycle[3.2.1]octane, spiro[4.5]decane, pinane, norpinane, norbornane, perhydronaphthalene, and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbamate of the formula —NH—CO—R", wherein R" comprises H, $C_{1-6}$ alkyl, aryl-$C_{1-6}$ alkyl, (heterocycle) $C_{1-6}$ alkyl, wherein said alkyl, aryl and heterocycle are defined as above, or aryl carbamate of the formula —NH—CO—Ar, wherein said aryl is defined as above, or heterocycle carbamate of the formula —NH—CO—heterocycle, wherein said heterocycle is defined as above, or carbocycle carbamate of the formula —NH—CO—carbocycle, wherein said carbocycle is defined as above, or sulfonamide of the formula —NH—S(O)$_n$R, wherein said n is 1 or 2, $R_2$, $R_3$, $R_4$, $R_5$, $R_6$ and $R_7$ are independently selected from the group consisting of H, halogen, CN, OH, SH, $NH_2$, $N_3$, $NO_2$, $CO_2R$, CONRR', $SO_3R$, $SO_2NRR'$, alkylcarbonyloxy, alkylcarbamate, $C_{1-6}$ alkyl, $C_{1-6}$ alkoxy, $C_{1-6}$ alkylsulphinyl, $C_{1-6}$ alkylsulphonyl, $C_{1-6}$ alkylamino, di($C_{1-6}$ alkyl)amino, $C_{1-6}$ alkylamino-$C_{1-6}$ alkyl, di($C_{1-6}$ alkyl)amino-$C_{1-6}$ alkyl, or cyclo($C_{3-6}$)alkyl, wherein said alkyl is straight-chained or branched, saturated or unsaturated, and is optionally substituted with one or more substituents selected from the group consisting of halogen, $N_3$, CN, $NO_2$, SR, OR, NRR', SOR, $SO_2R$, $SO_3R$, $SO_2NRR'$, COR, $CO_2R$ and CONRR', or aryl, aryl-$C_{1-6}$ alkyl, aryloxy, aryl-$C_{1-6}$ alkyloxy, arylsulphinyl, arylsulphonyl, aryl-$C_{1-6}$ alkylsulphinyl, aryl-$C_{1-6}$ alkylsulphonyl, arylcarbonyloxy, arylcarbamate, arylamino, di(aryl)amino, aryl-$C_{1-6}$ alkylamino, di(aryl-$C_{1-6}$ alkyl)amino, wherein said alkyl is defined as above; aryl comprises six membered aromatic carbocycles such as phenyl or a polycyclic aromatic hydrocarbon such as naphthyl, phenanthracenyl, indanyl, indenyl, and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or heterocycle, (heterocycle)$C_{1-6}$ alkyl, (heterocycle)oxy, (heterocycle)$C_{1-6}$ alkyloxy, (heterocycle)sulphinyl, (heterocycle)sulphonyl, heterocycle-$C_{1-6}$ alkylsulphinyl, heterocycle-$C_{1-6}$ alkylsulphonyl, (heterocycle)carbonyloxy, (heterocycle)amino, di(heterocycle)amino, [(heterocycle)$C_{1-6}$ alkyl]amino, di[(heterocycle)$C_{1-6}$ alkyl]amino, wherein said alkyl is defined as above; heterocycle comprises 3–8 membered heterocycles such as oxirane, aziridine, pyrrole, pyrroline, pyrrolidine, pyrrolidone, pyrrolindione, pyrazole, imidazole, imidazoline, triazole, (1,2,4)-triazine-3,5-dione, furan, tetrahydrofuran, thiophene, oxazole, thiazole, pyridine, pyrimidine, pyridazine, pyrazine, piperidine, piperazine, pyran, morpholine, azepine, or polycyclic systems such as indole, indoline, indolizine, isoindole, indazole, benzthiophene, isobenzthiophene, benzofuran, isobenzofuran, benzimidazole, benzoxazole, benzothiazole, benzotriazole, quinoline, isoquinoline, quinazoline, benzotriazine, flavone, phenanthridine, and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbocycle, carbocycle-$C_{1-6}$ alkyl, (carbocycle)oxy, (carbocycle)-$C_{1-6}$ alkyloxy, (carbocycle)carbonyloxy, (carbocycle)amino, di(carbocycle)amino, [(carbocycle)$C_{1-6}$ alkyl]amino, di[(carbocycle) $C_{1-6}$ alkyl]amino, wherein said alkyl is defined as above; carbocycle comprises 3–8 membered carbocycles such as cyclopropane, cyclobutane, cyclobutene, cyclopentane, cyclopentene, cyclopentadiene, cyclohexane, cycloheptane, cyclooctane, or polycyclic systems such as bicycle[1.1.0]butane, bicycle[3.2.1]octane, spiro[4.5]decane, pinane, norpinane, norbornane, perhydronaphthalene, and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR' or $R_2$ and $R_3$, $R_4$ and $R_5$, or $R_3$ and $R_4$ together form a non-aromatic 5–8 membered cyclic or heterocyclic rings;

$R_8$, $R_9$, $R_{10}$ and $R_{11}$ are independently selected from the group consisting of H, OH, $NH_2$, alkylcarbonyloxy, alkylcarbamate, $C_{1-6}$ alkyl, $C_{1-6}$ alkyloxy, $C_{1-6}$ alkylamino, di($C_{1-6}$ alkyl)amino, $C_{1-6}$ alkylamino-$C_{1-6}$ alkyl, di($C_{1-6}$ alkyl) amino-$C_{1-6}$ alkyl, cyclo($C_{3-6}$)alkyl, aryl, carbocyclic or heterocyclic, wherein said alkyl, aryl, carbocyclic and heterocyclic are defined above; $R_8$ and $R_9$ together, $R_{10}$ and $R_{11}$ together can independently form =O;

$R_{12}$ represents an optionally substituted pentose or hexose group or said pentose and/or hexose may be linked to form an oligosaccharide, or H, OH, $NH_2$, $SO_2NRR'$, $CO_2H$, CONRR', $C_{1-12}$ alkylcarbonyl, $C_{1-12}$ alkyloxycarbonyl, $C_{1-12}$ alkylcarbonyloxy, $C_{1-12}$ alkyl, $C_{1-12}$ epoxyalkyl, $C_{1-12}$ alkyloxy, $C_{1-6}$ alkyloxy- $C_{1-6}$ alkyl, $C_{1-6}$ alkylthio-$C_{1-6}$ alkyl, $C_{1-12}$ alkylamino, di($C_{1-12}$ alkyl)amino, $C_{1-6}$ alkylamino-$C_{1-6}$ alkyl, di($C_{1-6}$ alkyl)amino-$C_{1-6}$ alkyl, $C_{1-6}$ alkyloxy-$C_{1-6}$ alkylamino, di($C_{1-6}$ alkyloxy-$C_{1-6}$ alkyl)amino, $C_{1-6}$ alkylamino-$C_{1-6}$ alkyloxy, di($C_{1-6}$ alkylamino)-$C_{1-6}$ alkyloxy, cyclo($C_{3-6}$) alkyl, $C_{1-12}$ alkylsulphinyl, $C_{1-12}$ alkylsulphonyl, $C_{1-6}$ alkylsulphinyl-$C_{1-6}$ alkyl, $C_{1-6}$ alkylsulphonyl-$C_{1-6}$ alkyl, polyethyleneglycole (PEG), polyamine, wherein said alkyl is straight-chained or branched, saturated or unsaturated, and is optionally substituted with one or more substituents selected from the group consisting of halogen, $N_3$, CN, $NO_2$, SR, OR, NRR', SOR, $SO_2R$, $SO_3R$, $SO_2NRR'$, COR, $CO_2R$ and CONRR', or aryl, aryl-$C_{1-6}$ alkyl, aryloxy, aryl-$C_{1-6}$ alkyloxy, arylcarbonyloxy, arylamino, di(aryl)amino, aryl-$C_{1-6}$ alkylamino, di(aryl-$C_{1-6}$ alkyl)amino, arylsulphinyl, arylsulphonyl, arylsulphinyl-$C_{1-6}$ alkyl, arylsulphonyl-$C_{1-6}$ alkyl, wherein said alkyl is defined as above; aryl comprises six membered aromatic carbocycles such as phenyl or a polycyclic aromatic hydrocarbon such as naphthyl, phenanthracenyl, indanyl, indenyl, and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or heterocycle, (heterocycle)$C_{1-6}$ alkyl, (heterocycle)oxy, (heterocycle)$C_{1-6}$ alkyloxy, (heterocycle)carbonyloxy, (heterocycle)amino, di(heterocycle)amino, [(heterocycle)$C_{1-6}$ alkyl]amino, di[(heterocycle)$C_{1-6}$ alkyl]amino, wherein said alkyl is defined as above; heterocycle comprises 3–8 membered heterocycles such as oxirane, aziridine, pyrrole, pyrroline, pyrrolidine, pyrrolidone, pyrrolindione, pyrazole, imidazole, imidazoline, triazole, (1,2,4)-triazine-3,5-dione, furan, tetrahydrofuran, thiophene, oxazole, thiazole, pyridine, pyrimidine, pyridazine, pyrazine, piperidine, piperazine, pyran, morpholine, azepine, or polycyclic systems such as indole, indoline, indolizine, isoindole, indazole, benzthiophene, isobenzthiophene, benzofuran, isobenzofuran, benzimidazole, benzoxazole, benzothiazole, benzotriazole, quinoline, isoquinoline, quinazoline, benzotriazine, flavone, phenanthridine, and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbocycle, (carbocycle)$C_{1-6}$ alkyl, (carbocycle)oxy, (carbocycle)$C_{1-6}$ alkyloxy, (carbocycle)carbonyloxy, (carbocycle)amino, di(carbocycle)amino, [(carbocycle)$C_{1-6}$ alkyl]amino, di[(carbocycle)$C_{1-6}$ alkyl]amino, wherein said alkyl is defined as above; carbocycle comprises 3–8 membered carbocycles such as cyclopropane, cyclobutane, cyclobutene, cyclopentane, cyclopentene, cyclopentadiene, cyclohexane, cycloheptane, cyclooctane, or polycyclic systems such as bicycle[1.1.0]butane, bicycle[3.2.1]octane, spiro[4.5]decane, pinane, norpinane, norbornane, perhydronaphthalene, and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbamate of the formula —NH—CO—R", wherein R" comprises H, $C_{1-6}$ alkyl, aryl-$C_{1-6}$ alkyl, heterocycle-$C_{1-6}$ alkyl, wherein said alkyl, aryl and heterocycle are defined as above, or aryl carbamate of the formula —NH—CO—Ar, wherein said aryl is defined as above, or heterocycle carbamate of the formula —NH—CO-heterocycle, wherein said heterocycle is defined as above, or carbocycle carbamate of the formula —NH—CO-carbocycle, wherein said carbocycle is defined as above, or sulfonamide of the formula —NH—S(O)$_n$R, wherein said n is 1 or 2, $X_1$, $X_2$ and $X_3$ are independently selected from the group consisting of O, N, S, NH, (CH)$_n$, (CH$_2$)$_n$, CO, wherein said n is 1, 2 or 3, and the hydrogen atom in NH, CH, CH$_2$ is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', Z is selected from the group consisting of CH$_2$, NH, O, S; R and R' are independently selected from the group consisting of H, $C_{1-12}$ alkyl, aryl, heterocyclic, carbocyclic, and cyclo($C_{3-6}$)alkyl, wherein said alkyl is optionally substituted with one or more substituents selected from the group consisting of halogen, OH, NH$_2$, $N_3$, SH, CN, $CO_2$H, $CO_2$($C_{1-3}$ alkyl), S($C_{1-3}$ alkyl), O($C_{1-3}$ alkyl), NH($C_{1-3}$ alkyl), NH($C_{1-3}$ alkyl)$_2$, and is saturated or unsaturated; or R and R' together with the nitrogen atom to which they are attached form a non-aromatic 5–8 membered heterocycle containing one or two of the same or different heteroatoms selected from the group consisting of O, N, and S;

or a pharmaceutically acceptable salt thereof.

Pentoses in the compounds of the invention include, without limitation, ribose, arabinose, xylose, 2-deoxyribose, 2,3-dideoxypentofuranose, 2,3-didehydro-2,3-dideoxypentofuranose, and derivatives thereof. Hexoses in the compounds of the invention include, without limitation, allose, glucose, mannose, galactose, glucosamine, galactosamine, 2-deoxyglucose, 4-O-methylglucose, rhamnose, and glucuronic acid, and derivatives thereof. $R_{12}$ can include pentoses and hexoses that are linked together to form oligosaccharides such as 6-O-α-D-2-deoxy-4-aminoribosyl-β-D-4-methylglucopyranose disaccharide. The pentoses and hexoses may be optionally substituted as follows. The hydrogen and hydroxy groups of the pentose and hexose groups may be independently replaced with one or more substituents independently selected from H, halogen, R, $N_3$, CN, $NO_2$, SR, OR, NRR', SOR, $SO_2R$, $SO_3R$, $SO_2NRR'$, COR, $CO_2R$, CONRR', alkylcarbonyloxy, alkylcarbamate, $C_{1-6}$ alkyl, $C_{1-6}$ alkoxy, $C_{1-6}$ alkylsulphinyl, $C_{1-6}$ alkylsulphonyl, $C_{1-6}$ alkylamino, di($C_{1-6}$ alkyl)amino, $C_{1-6}$ alkylamino-$C_{1-6}$ alkyl, di($C_{1-6}$ alkyl)amino-$C_{1-6}$ alkyl, cyclo($C_{3-6}$)alkyl, aryl, carboncyclic, and heterocyclic, wherein said alkyl, aryl, carbocyclic and heterocyclic groups are as defined above. In addition, one or more hydroxyl groups of pentose and hexose may be derivatized or oxidized to form, for example, esters, amides, or ethers, or reduced to form unsaturated groups. One or more ring atoms of pentose and hexose may also be optionally replaced with CH$_2$, CHR, CR$_2$, O, S, NH, or NR.

Another object of the invention is to provide a method of inhibiting topoisomerase I activity in a mammal comprising administering to a mammal in need of inhibition of topoisomerase I activity an effective amount of a compound of the formula I or II.

Yet another object of the invention is to provide compositions for inhibiting topoisomerase I activity in a mammal in need of inhibition of topoisomerase I activity an effective amount of at least one compound of the formulas I and II.

These and other objects of the invention will be clear in light of the detailed description below.

DETAILED DESCRIPTION OF THE INVENTION

The description of the invention herein should be construed in congruity with the laws and principals of chemical bonding. It is to be understood that the present invention includes any and all possible stereoisomers, geometric isomers, diastereoisomers, enantiomers and anomers, unless a particular description specifies otherwise.

The compounds of this invention can exist in the form of pharmaceutically acceptable salts. Such salts include addition salts with inorganic acids such as hydrochloric acid and sulfuric acid, and with organic acids such as acetic acid, citric acid, methanesulfonic acid, toluenesulfonic acid, tartaric acid amd maleic acid. Further, in case the compounds of this invention contain an acidic group, the acidic group can exist in the form of an alkali metal salt such as a potassium salt and a sodium salt; an alkaline earth metal salts such as magnesium salt and calcium salt; and salts with organic bases such as triethylammonium salt and an arginine salt. The compounds of the present invention may be hydrated ot non-hydrated.

The compounds disclosed in the present invention are useful as antitumor agents for the treatment and/or prevention of cancer, either alone or with a carrier. Cytotoxic agents are often employed as anticancer agents to control or eradicate tumors. Topo I poisons are useful cytotoxic agents, and two Topo I poisons related to camptothecin, Camptosar and Hycamtin (topotecan) are currently used clinically for the treatment of tumors. Indolocarbazoles are a different class of Topo I poison that represent useful agents for the treatment of tumors. In particular, Topo I-poisoning compounds disclosed in this invention were shown to be highly cytotoxic against human ovarian and prostate tumor cells.

Indolocarbazole analogues of this invention may be formulated as a solution of lyophilized powders for parenteral administration, including, but not limiting to, intravenous, cutaneous, subcutaneous, intramuscular and intraperitoneal routes. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxycellulose, acacia, polyethylene glycol, mannitol, sodium chloride, or sodium acetate.

Alternatively, the compounds of the present invention may be encapsulated, tableted, or incorporated into an emulsion (oil-in-water or water-in-oil) syrup for oral administration. The dosage forms can be pills, powders, granules, elixirs, tinctures and suspensions, and can be designed as a sustained release or timed release. Pharmaceutically acceptable solids or liquid carriers, which are generally known in the pharmaceutical formulary arts, may be added to enhance or stabilize the composition, or to facilitate preparation of the composition. Solid carriers include starch (corn or potato), lactose, calcium sulfate dihydrate, terra alba, croscarmellose sodium, magnesium stearate or stearic acid, talc, pectin, acacia, agar, gelatin, maltodextrins and microcrystalline cellulose, or colloidal silicon dioxide. Liquid carriers include syrup, peanut oil, olive oil, corn oil, sesame oil, saline, and water. The carrier may also include a sustained release material such as glyceryl monostearate or glyceryl distearate, alone or with a wax. The amount of solid carrier varies but, preferably, will be between about 10 mg to about 1 g per dosage unit.

In addition, compounds of this invention may be given by inhalation, intranasal, rectal, vaginal, urethral, ocular, transdermal, transpulmonary, mucosal, transmucosal, topical, intratumoral and irrigation administration.

One aspect of the present invention involves administration of the compounds of the present invention, or pharmaceutically acceptable salts or solvates thereof, to a mammal implanted with a tumor or susceptible to cancer formation. The dosage ranges for administration of indolocarbazole analogues disclosed in this invention are those to produce the desired affect. The dosage will generally vary with age, body weight, extent of the disease, and contraindications, if any. The dosage will also be determined by the existence of any adverse side effects that may accompany the compounds. It is always desirable, whenever possible, to keep adverse side effects to a minimum. One skilled in the art can easily determine the appropriate dosage, scheduling, and method of administration for the exact formulation of the composition being used in order to achieve the desired effective concentration in the individual patient. However, the dosage can vary from between about 1 mg/kg/day to about 500 mg/kg/day, and preferable from between about 1 mg/kg/day to about 50 mg/kg/day.

Preferred compounds of formula I include those wherein Z is NH.

Preferred compounds of formula I include those wherein $R_2$, $R_3$, $R_4$ and $R_5$ are each H.

Preferred compounds of formula I include those wherein $R_2$, $R_3$ and $R_4$ are each H and $R_5$ is OH or F.

Preferred compounds of formula I include those wherein $R_2$, $R_3$ and $R_5$ are each H, and $R_4$ is OH, $NH_2$, Br, or F.

Preferred compounds of formula I include those wherein $R_2$ is OH, $NH_2$, or F, and $R_3$, $R_4$ and $R_5$ are each H.

Preferred compounds of formula I include those wherein $R_2$ and $R_5$ are both H, and $R_3$ and $R_4$ are both OH.

Preferred compounds of formula I include those wherein $R_2$, $R_4$, and $R_5$ are each H, and $R_3$ is $CH_3$, $N_3$, $NO_2$, $NH_2$, Br, or F.

Preferred compounds of formula I include those wherein $R_2$ and $R_5$ are both H, and $R_3$ and $R_4$ are both F.

Preferred compounds of formula I include those wherein $R_2$ and $R_3$ are both F, and $R_4$ and $R_5$ are both H.

Preferred compounds of formula I include those wherein $R_2$ is H, and $R_3$, $R_4$, and $R_5$ are each F.

Preferred compounds of formula I include those wherein $R_4$ is H, and $R_2$, $R_3$, and $R_5$ are each F.

Preferred compounds of formula I include those wherein $R_2$, $R_3$, $R_4$, and $R_5$ are each F.

Preferred compounds of formula I include those wherein $R_3$ and $R_5$ are both H, $R_2$ is OH and $R_4$ is F.

Preferred compounds of formula I include those wherein $R_3$ and $R_4$ are both H, $R_2$ is OH and $R_5$ is F.

Preferred compounds of formula I include those wherein $R_2$ and $R_5$ are both H, $R_3$ is OH and $R_4$ is F.

Preferred compounds of formula I include those wherein $R_2$ and $R_5$ are both H, $R_3$ is F and $R_4$ is OH.

Preferred compounds of formula I include those wherein $R_{12}$ is selected from the group consisting of:

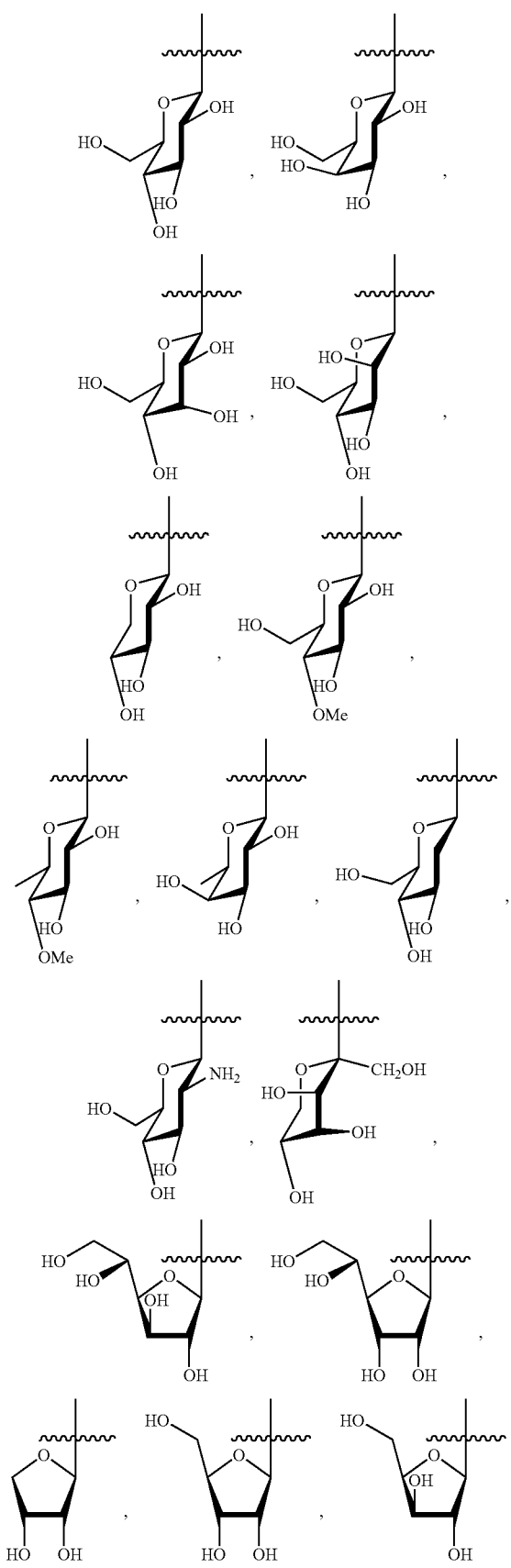

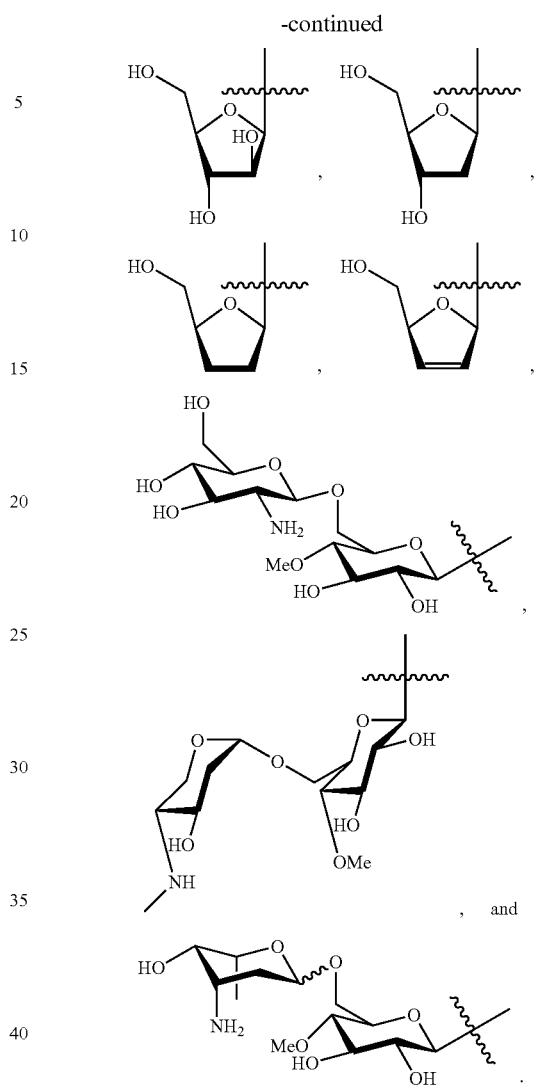

Preferred compounds of formula I include those wherein $R_8$ and $R_9$ together form =O.

Preferred compounds of formula I include those wherein $R_{10}$ and $R_{11}$ together form =O.

Preferred compounds of formula I include those wherein $R_1$ is H.

Preferred compounds of formula I include those wherein $X_1$ and $X_3$ are both O and $X_2$ is $(CH_2)_n$, wherein n=1, 2, or 3.

Preferred compounds of formula I include those wherein when $R_{12}$ is β-D-glucopyranosyl, $R_8$ and $R_9$ together and $R_{10}$ and $R_{11}$ together form =O, $X_1$ and $X_3$ are O and $X_2$ is $(CH_2)_n$ (n=1, 2, 3), then $R_2$, $R_4$, $R_5$, $R_6$ and $R_7$ are not H at the same time.

Preferred compounds of formula II include those wherein Z is NH.

Preferred compounds of formula II include those wherein $R_2$, $R_3$, $R_4$ and $R_5$ are each H.

Preferred compounds of formula II include those wherein $R_2$, $R_3$ and $R_4$ are each H and $R_5$ is OH or F.

Preferred compounds of formula II include those wherein $R_2$, $R_3$ and $R_5$ are each H, and $R_4$ is OH, $NH_2$, Br, or F.

Preferred compounds of formula II include those wherein $R_2$ is OH, $NH_2$, or F, and $R_3$, $R_4$ and $R_5$ are each H.

Preferred compounds of formula II include those wherein $R_2$ and $R_5$ are both H, and $R_3$ and $R_4$ are both OH.

Preferred compounds of formula II include those wherein $R_2$, $R_4$, and $R_5$ are each H, and $R_3$ is $CH_3$, $N_3$, $NO_2$, $NH_2$, Br, or F.

Preferred compounds of formula II include those wherein $R_2$ and $R_5$ are both H, and $R_3$ and $R_4$ are both F.

Preferred compounds of formula II include those wherein $R_2$ and $R_3$ are both F, and $R_4$ and $R_5$ are both H.

Preferred compounds of formula II include those wherein $R_2$ is H, and $R_3$, $R_4$, and $R_5$ are each F.

Preferred compounds of formula II include those wherein $R_4$ is H, and $R_2$, $R_3$, and $R_5$ are each F.

Preferred compounds of formula II include those wherein $R_2$, $R_3$, $R_4$, and $R_5$ are each F.

Preferred compounds of formula II include those wherein $R_3$ and $R_5$ are both H, $R_2$ is OH and $R_4$ is F.

Preferred compounds of formula II include those wherein $R_3$ and $R_4$ are both H, $R_2$ is OH and $R_5$ is F.

Preferred compounds of formula II include those wherein $R_2$ and $R_5$ are both H, $R_3$ is OH and $R_4$ is F.

Preferred compounds of formula II include those wherein $R_2$ and $R_5$ are both H, $R_3$ is F and $R_4$ is OH.

Preferred compounds of formula II include those wherein $R_{12}$ is selected from the group consisting of:

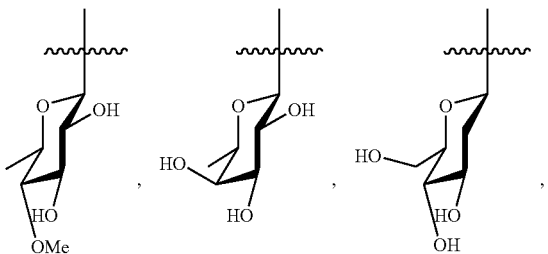

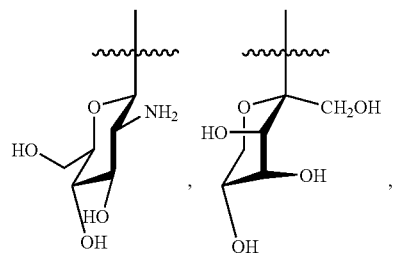

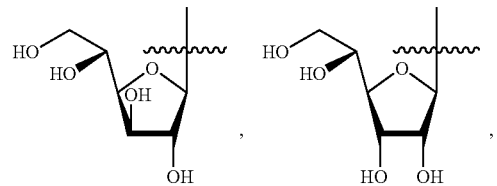

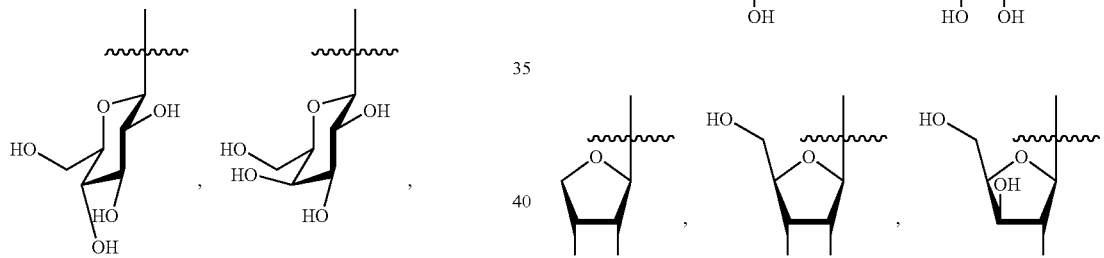

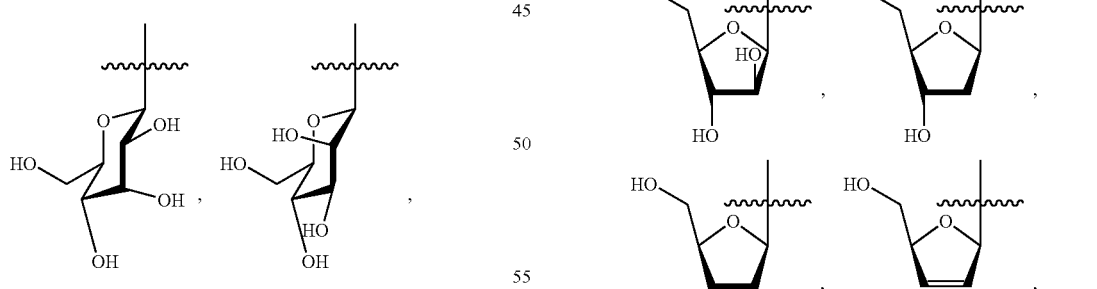

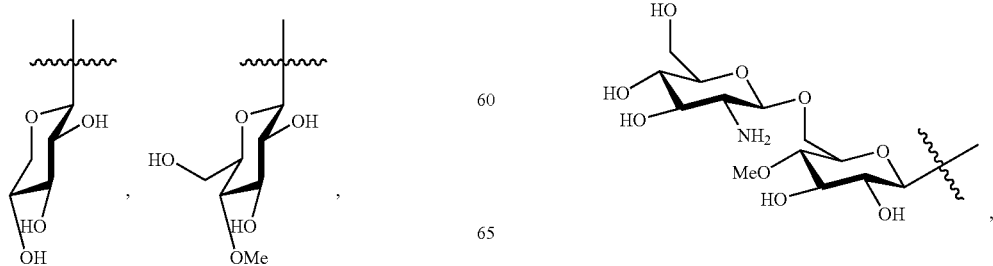

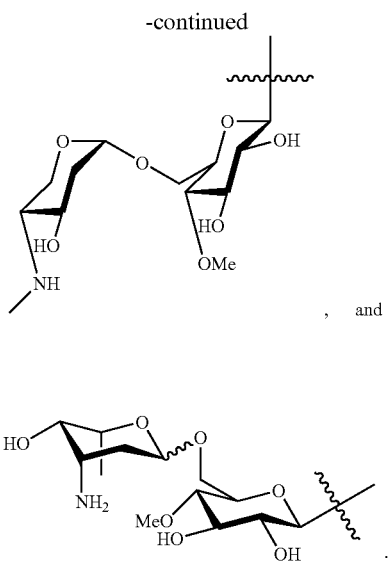

, and

Preferred compounds of formula II include those wherein $R_8$ and $R_9$ together form =O.

Preferred compounds of formula I include those wherein $R_{10}$ and $R_{11}$ together form =O.

Preferred compounds of formula II include those wherein $R_1$ is H.

Preferred compounds of formula II include those wherein $X_1$ and $X_3$ are both O and $X_2$ is $(CH_2)_n$, wherein n=1, 2, or 3.

Preferred compounds of formula II include those wherein when $R_{12}$ is β-D-glucopyranosyl, $R_8$ and $R_9$ together and $R_{10}$ and $R_{11}$ together form =O, $X_1$ and $X_3$ are O and $X_2$ is $(CH_2)_n$ (n=1, 2, 3), then $R_2$, $R_4$, $R_5$, $R_6$ and $R_7$ are not H at the same time.

One skilled in the art will recognize that modifications may be made in the present invention without deviating from the spirit or scope of the invention. The invention is illustrated further by the following examples, which are not to be construed as limiting the invention in spirit or scope to the specific procedures or compositions described in them.

Synthesis of Target Molecules

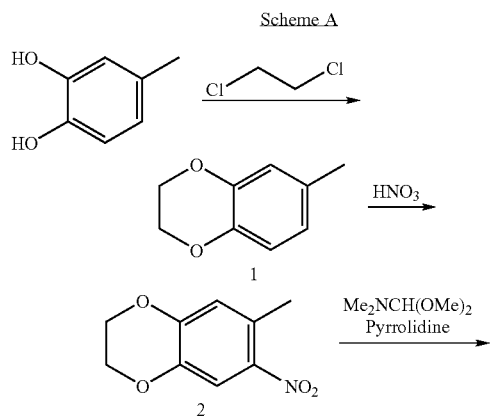

The required 5,6-indolodioxan and 5,6-indolodioxole precursors can be prepared starting from 4-methylcatechol, as illustrated in Scheme A for 5,6-ethylenedioxyindole (4). Protection of the ortho-dihydroxy function was achieved using 1,2-dibromoethane, dichloromethane, and acetone, respectively. Nitration using fuming nitric acid followed by indole formation using the Batcho-Leimgruber protocol[17] afforded the desired indoles.

Construction of indolocarbazole analogues can be conducted as illustrated in Scheme B for Ia. N-Benzyloxymethyl-3,4-dibromomaleimide was prepared as previously described.[18] Reaction with an appropriate indole, which had been pre-treated using an organometallic, preferably but not limited to methylmagnesium halide or lithium hexamethyldisilazide, afforded the bromoindolomaleimide intermediates represented by 5. Glucosidation at the indole nitrogen was achieved with 2,3,4,6-tetra-O-benzyl-D-glucose under Mitsunobu conditions[14] (3 equivalents each of the glucose, $PPh_3$, and diisopropylazodicarboxylate (DIAD), followed by reversed-phase purification to afford 6. Introduction of the second indole unit was conducted under conditions similar to introduction of the first indole unit, providing the bis-indolylmaleimides represented by 7. Oxidative cyclization of the bis-indolylmaleimides was achieved using either palladium(II) trifluoroacetate in DMF, or via photochemical cyclization, providing indolocarbazoles represented by 8. Others[19] reported oxidative cyclization using alternative reagents such as $CuCl_2$ and $PdCl_2$, but these failed to catalyze the reaction in our hands. Hydrogenolysis of the protective groups (palladium hydroxide, HOAc) afforded the 6-N-hydroxymethyl derivatives represented by 9, which were readily converted to the desired final products, represented by Ia, using ammonium acetate in methanol. All compounds provided spectral and analytical characteristics ($^1$H NMR, $^{13}$C NMR, MS and elemental analysis) consistent with the targeted structures.

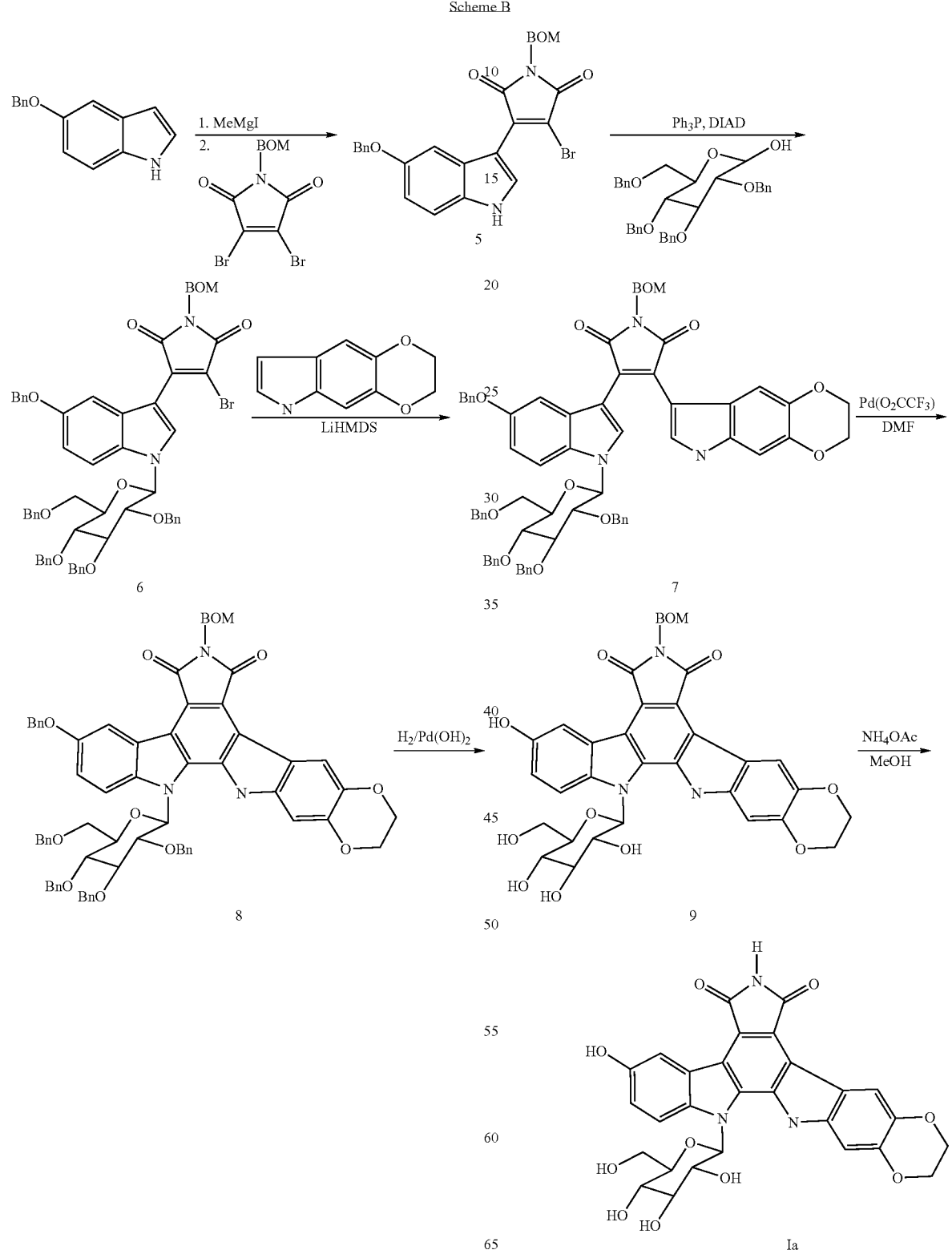

The same synthetic strategy described in Scheme B can be extended for the preparation of compounds of general formula I and II, as illustrated in Scheme C and Scheme D.
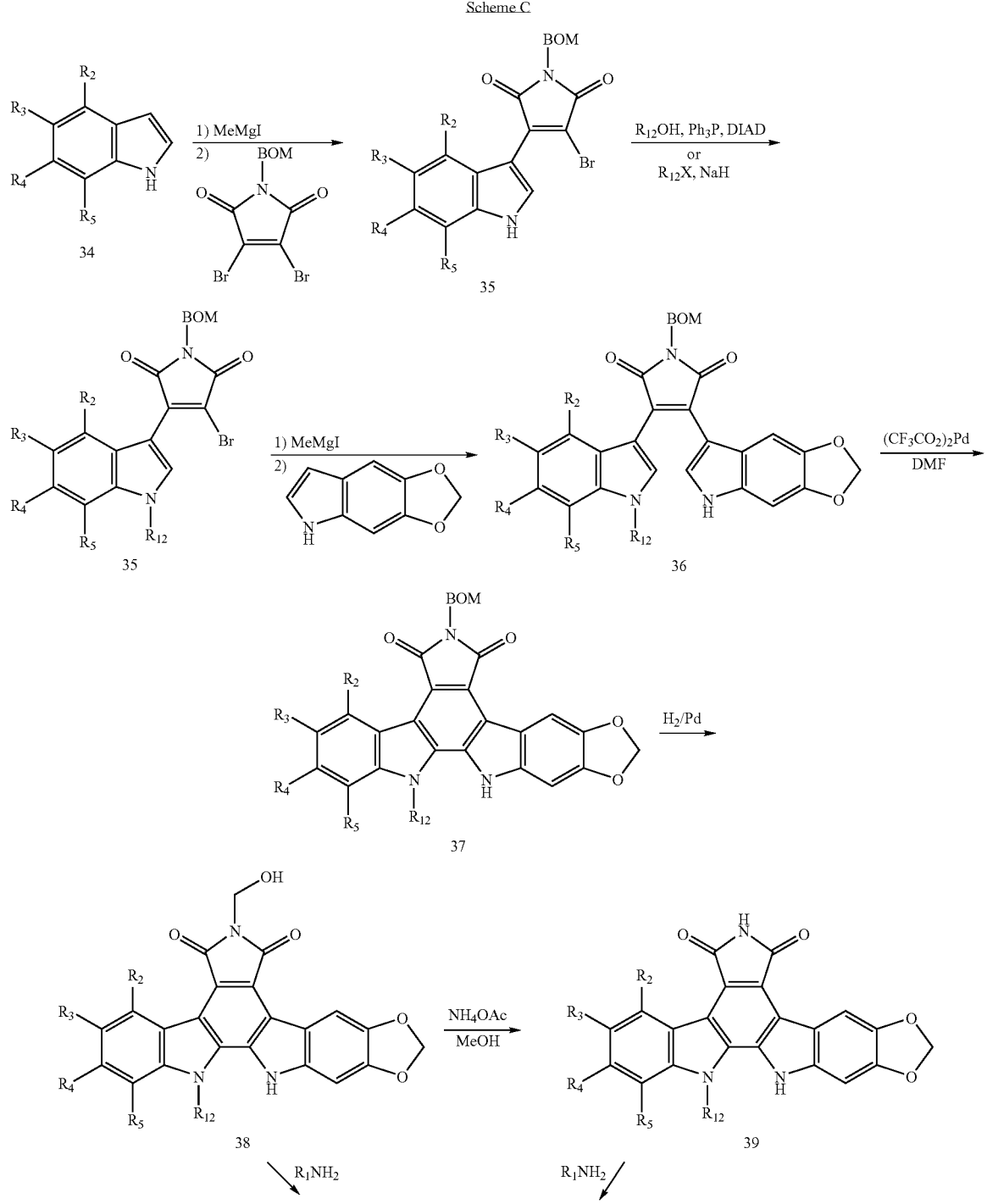
Scheme C

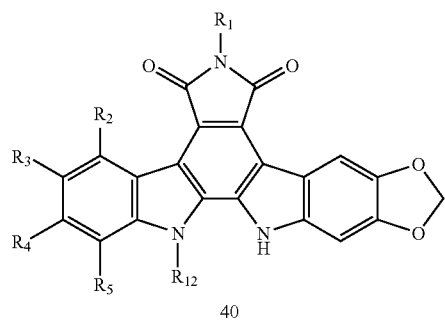
Scheme D
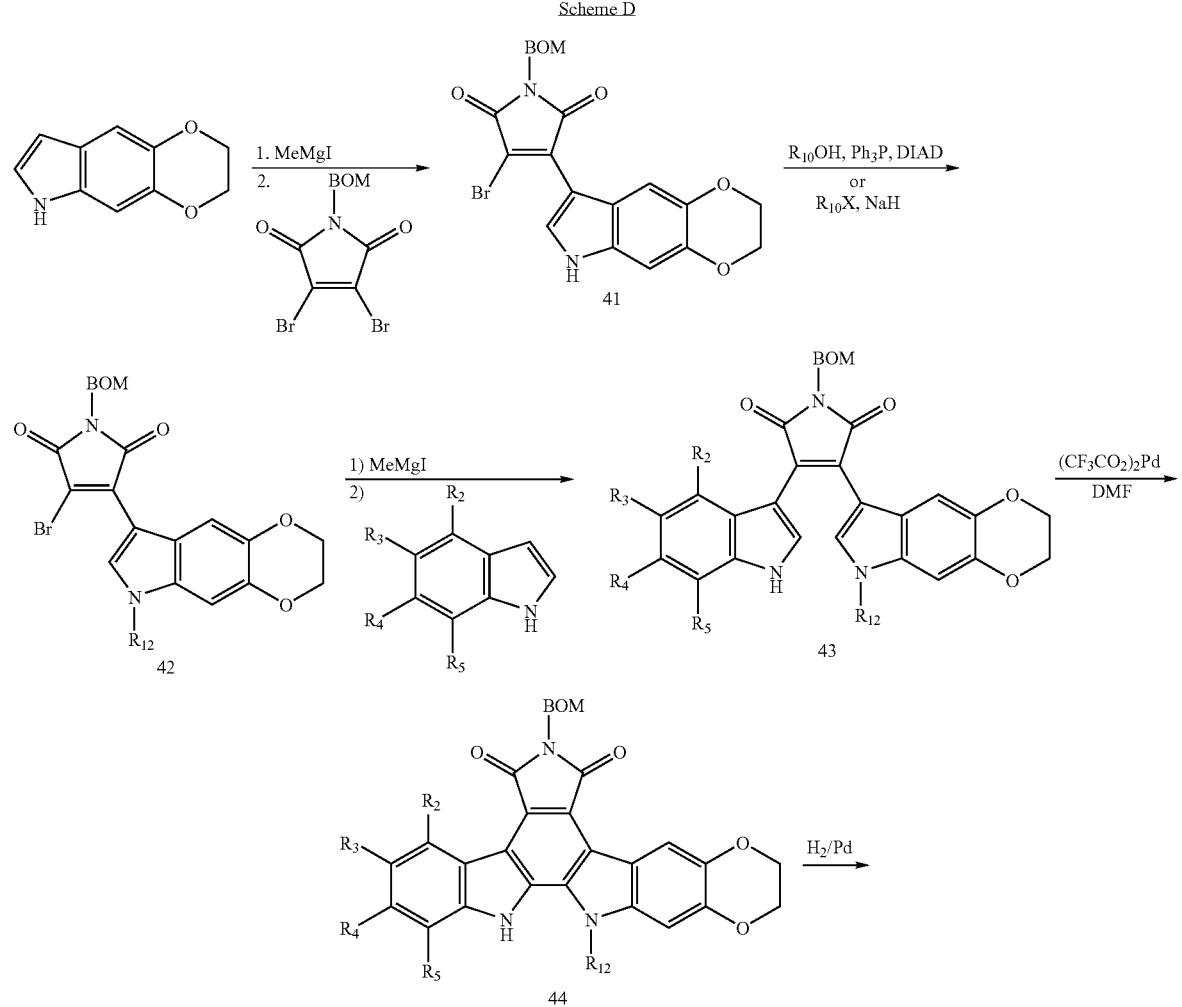

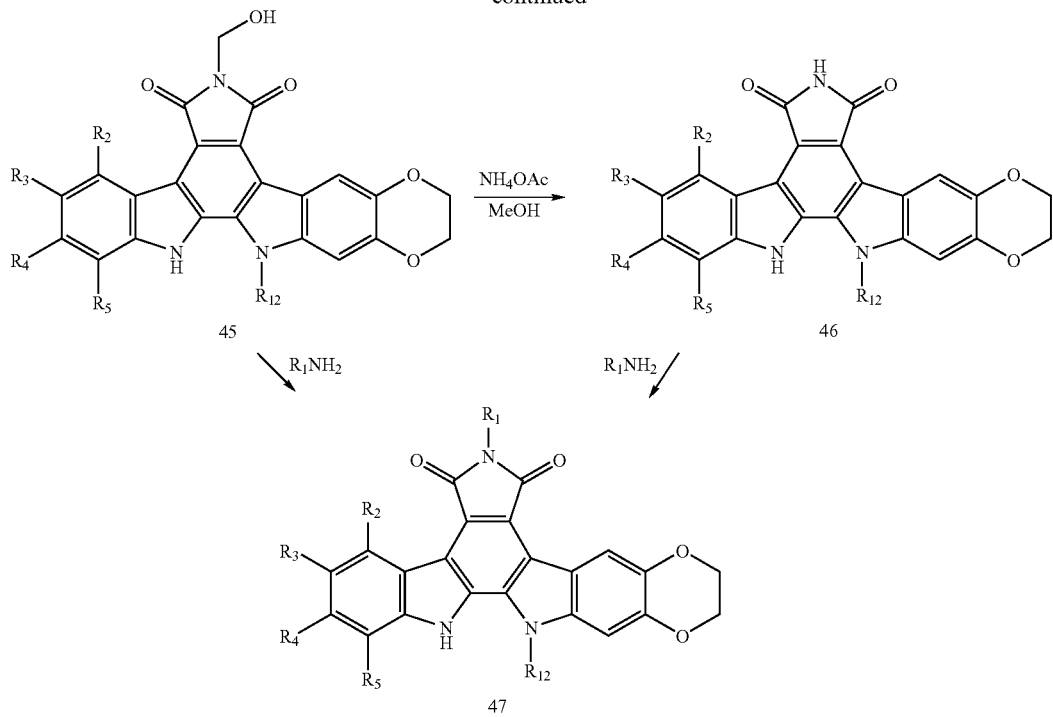
A versatile method has been reported for the synthesis of indoles containing both hydroxyl and fluorine[20] (Scheme E). Examples of indoles are shown in FIG. 1.
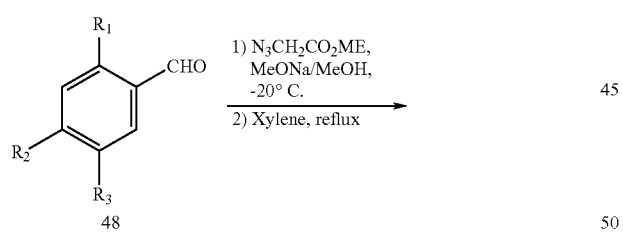
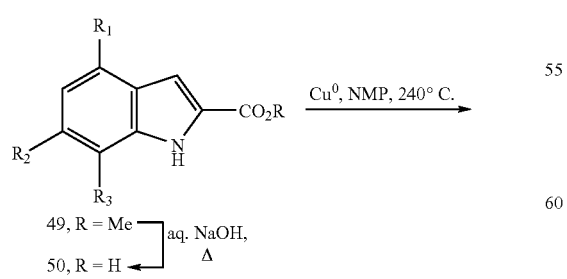
-continued
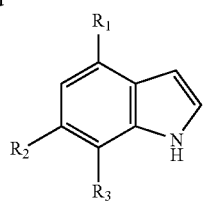
51o, $R_1 = R_3 = H$, $R_2 = F$
51w, $R_1 = OBn$, $R_2 = F$, $R_3 = H$
51x, $R_1 = OBn$, $R_2 = H$, $R_3 = F$
FIG. 1. Examples of Indole Derivatives
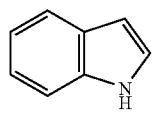
51a
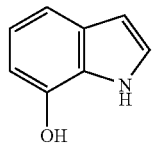
51b
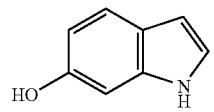
51c -continued
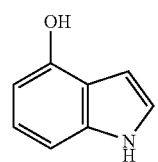 51d
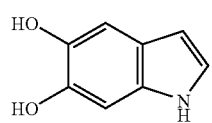 51e
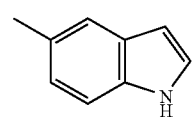 51f
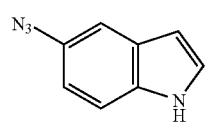 51g
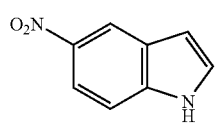 51h
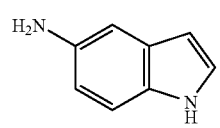 51i
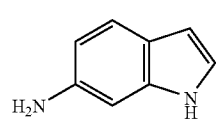 51j
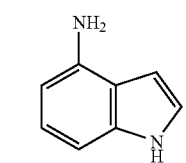 51k
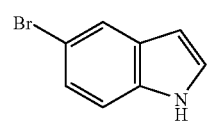 51l
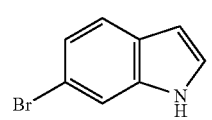 51m
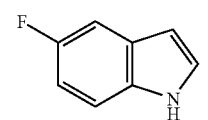 51n
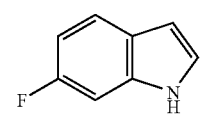 51o
-continued
 51p
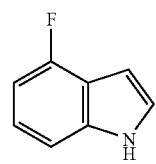 51q
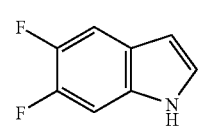 51r
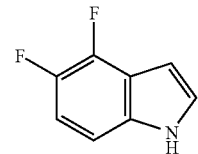 51s
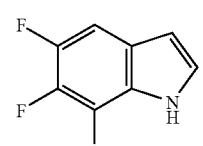 51t
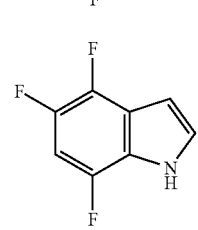 51u
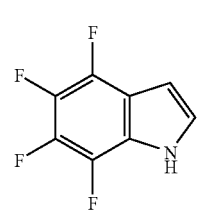 51v
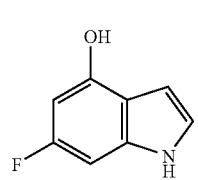 51w
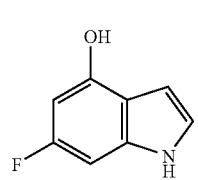 51w -continued
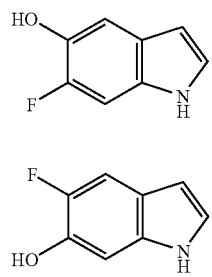
51y
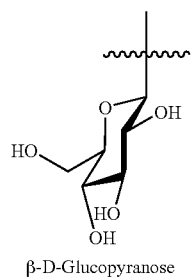
51z
The representative pentose and hexose moieties of $R_{12}$ are listed in FIG. 2.
FIG. 2. Examples of Pentose and Hexose Moieties
(a)
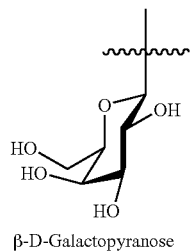
β-D-Glucopyranose
(b)
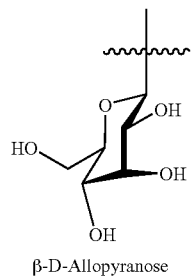
β-D-Galactopyranose
(c)
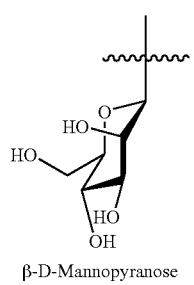
β-D-Allopyranose
(d)
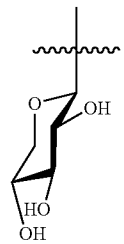
β-D-Mannopyranose
-continued
(e)
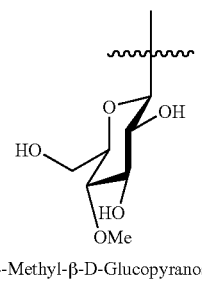
β-D-Xylopyranose
(f)
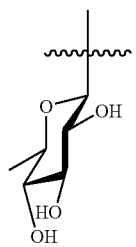
4-Methyl-β-D-Glucopyranose
(g)
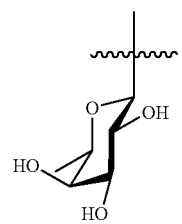
6-Deoxy-β-D-glucopyranose
(h)
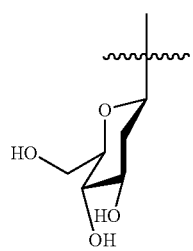
6-Deoxy-β-D-Galactopyranose(β-D-Fucose)
(i)
2-Deoxy-β-D-glucopyranose -continued
(j)
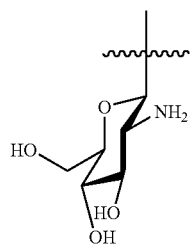
2-Amino-2-deoxy-β-D-glucopyranose
(k)
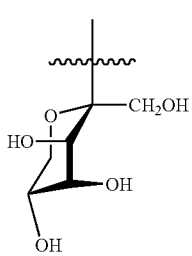
β-D-Fructopyranose
(l)
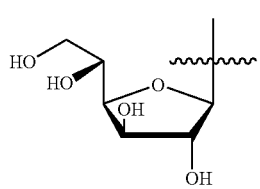
β-D-Glucofuranose
(m)
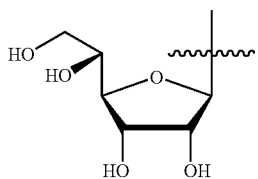
β-D-Allofuranose
(n)
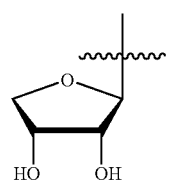
β-D-Erythrose
(o)
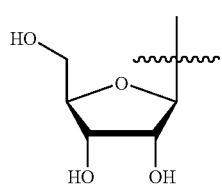
Ribofuranose
-continued
(p)
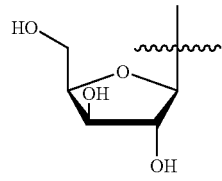
β-D-Xylofuranose
(q)
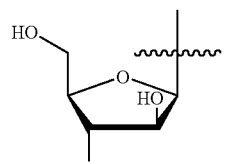
β-D-Arabinofuranose
(r)
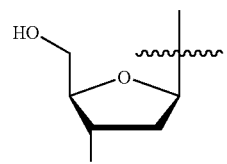
2-Deoxy-β-D-ribofuranose
(s)
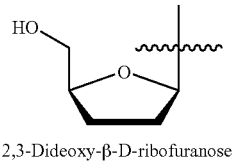
2,3-Dideoxy-β-D-ribofuranose
(t)
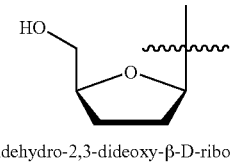
2,3-Didehydro-2,3-dideoxy-β-D-ribofuranose
(u)
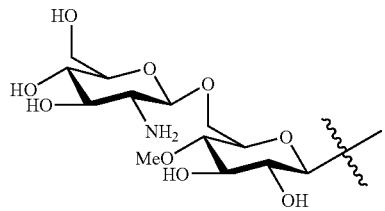
6-O-β-D-2-amino-2-deoxy-glucosyl-β-D-4-methylglucopyranose disaccharide -continued

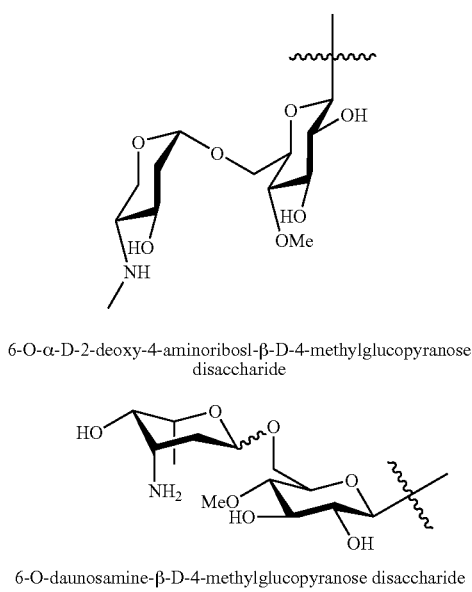

6-O-α-D-2-deoxy-4-aminoribosl-β-D-4-methylglucopyranose disaccharide (v)

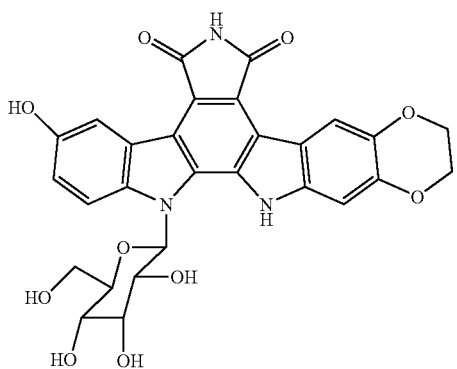

6-O-daunosamine-β-D-4-methylglucopyranose disaccharide (w)

The following examples are illustrative of the invention but do not serve to limit its scope.

EXAMPLE 1

Synthesis of 2,3-ethylenedioxy-9-hydroxy-12-(β-D-glucopyranosyl)-6,7,12,13-tetrahydroindolo[2,3-a]pyrrolo[3,4-c]carbazole-5,7-dione (Ia)

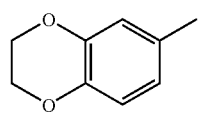

Step A: Preparation of 6-methyl-1,4-benzodioxane (1)

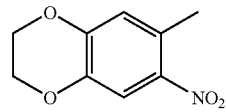

A mixture of 4-methylcatechol (33.04 g, 266.1 mmol), 1,2-dibromoethane (100 g, 532.3 mmol), $K_2CO_3$ (75.4 g, 545.5 mmol) and sodium iodide (0.2 g, 1.33 mmol) in ethylene glycol (500 mL) was heated to 130° C. under nitrogen for five hours. The solution was allowed to cool to ambient temperature and stirred overnight. After the mixture was filtered through celite, the solution was diluted with brine (800 mL) and extracted with organic solvents ($CH_2Cl_2$/hexane/EtOAc: 1:3:1,3×500 mL). The organic layer was dried over $Na_2SO_4$, filtered and concentrated to provide a crude oil. Flash silica gel chromatography eluting with hexane (100%) gradient to ether/hexane (8:2) afforded the title intermediate as a colorless oil 20.0 g (50%).

Step B: Preparation of 6-methyl-7-nitro-1,4-benzodioxane (2)

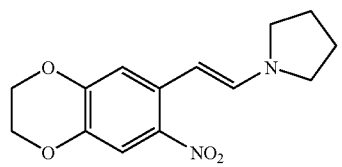

To a solution of 1 (20.0 g, 133.3 mmol) in acetic acid (135 mL) was added a solution of fuming $HNO_3$ (10 mL) in acetic acid (50 mL) dropwise over 30 minutes. The mixture was stirred at ambient temperature for 10 minutes, then poured into a beaker containing ice to give a crystalline precipitate, which was collected by vacuum filtration and washed with water to afford the product (25.8 g, 99.2%) as an off-white solid.

Step C: Preparation of (E)-4,5-ethylenedioxy-2-nitro-1-pyrrolidinostyrene (3)

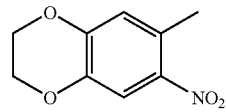

A solution of 2 (19.5 g, 100 mmol), N,N-dimethylformamide dimethyl acetal (23.63 g, 198.3 mmol) and pyrrolidine (14.1 g, 198.3 mmol) was heated to 110° C. and stirred for 24 hours under nitrogen. The reaction mixture was cooled, and 250 mL absolute methanol was added. The product crystallized as a bright red solid. Recovery by suction filtration afforded the product (24.3 g, 88.0%).

Step D: Preparation of 4,5-ethylenedioxyindole (4)

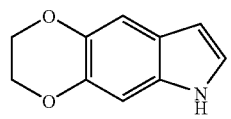

To a solution of 3 (24.0 g, 87.0 mmol) in methanol and THF (240 mL, 1:1) was added Raney nickel (2.0 mL) and hydrazine hydrate (3×3.6 mL, 348 mmol) every half hour at ambient temperature under nitrogen. Then, the solution was heated at 45° C. for two hours. The mixture was cooled to room temperature and the catalyst is removed by filtration through a bed of Celite and washed three times with methylene chloride. The filtrate was evaporated and the residue dried by evaporating with toluene (100 mL) to give a crude oil. Flash silica gel column purification eluting with hexane (100%) gradient to ethyl acetate/hexane (40/60%) afforded the title intermediate as an off-white solid (7.0 g, 46.1%).

Step E: Preparation of 2-bromo-3-(5-benzyloxy-1H-indol-3-yl)-N-benzyloxymethylmaleimide (5)

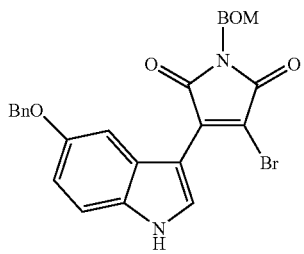

To a solution of 5-benzyloxyindole (8.93 g, 40 mmol) in benzene (150 mL) was added methylmagnesium iodide (14.7 mL, 44.0 mmol, 3 M in ether) at 0° C. The solution was stirred for one hour, and then a solution of N-benzyloxymethyl-3,4-dibromomaleimide (15.0 g, 40 mmol) in benzene (50 mL) and THF (100 mL) was added. The reaction mixture was stirred at 0° C. for 30 minutes and then warmed to room temperature and stirred for one hour. The mixture was diluted with EtOAc (350 mL) then washed with HCL (150 mL, 0.3 N), NaHCO₃ (200 mL) and H₂O (200 mL). The organic layer was dried over Na₂SO₄, filtered and concentrated. Crystallization of the crude oil with methanol afforded the title intermediate as a yellow solid (12.50 g, 66.0%).

Step F: Preparation of 2-bromo-3-[5-benzyloxy-1-(2,3,4,5-tetra-O-benzyl-β-D-glucopyranosyl)-1H-indol-3-yl]-N-benzyloxymethylmaleimide (6)

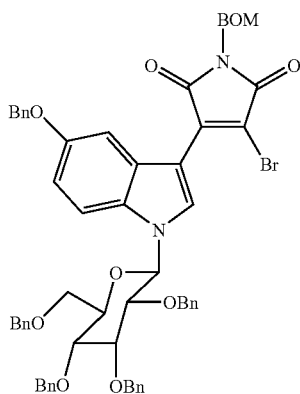

A solution of 5(15.0 g, 29.0 mmol), 2,3,4,5-tetra-O-benzyl-D-glucopyranose (47.02 g, 87.0 mmol) and triphenylphosphine (22.8 g, 87.0 mmol) in THF (800 mL) was cooled to −78° C. Diisopropylazodicarboxylate (17.14 mL, 87.0 mmol) was added dropwise, maintaining the temperature at −78° C., and then stirred for three hours. The solution was warmed to 0° C. with the aid of an ice-water bath and stirring was continued for two hours. The mixture was diluted with EtOAc (1200 mL), washed with HCl , brine, and H₂O. The organic layer was dried over Na₂SO₄, filtered and concentrated. The crude mixture was applied to a reversed-phase Biotage cartridge and eluted with a CH₃CN/H₂O (50/50) gradient to CH₃CN (100%) afforded the title intermediate as a yellow solid 22.3 g (74.0%).

Step G: Preparation of 3-(4,5-ethylenedioxy-1H-indol-3-yl)-4-[5-benzyloxy-1-(2,3,4,5-tetra-O-benzyl-β-D-glucopyranosyl)-1H-indol-3-yl]-N-benzyloxymethyl maleimide (7)

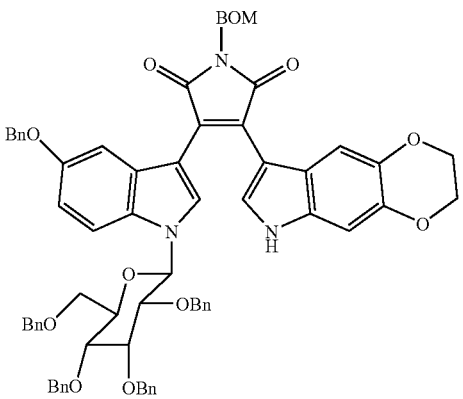

To a solution of 4 (303.2 mg, 1.73 mmol) in THF (35 mL) was added lithium hexamethyldisilazide (LiHMDS, 3.46 mL, 3.46 mmol, 1 M in THF) at 0° C., and the resulting solution stirred for 40 minutes. A solution of 6 in THF (20 mL) was added slowly to the above mixture, followed by stirring for 20 minutes at 0° C. The mixture was diluted with EtOAc (300 mL), washed with HCl (2 M), NaHCO₃, brine, and H₂O. The organic layer was dried over Na₂SO₄, filtered and concentrated to give a crude mixture. Flash silica gel chromatography eluting with a hexane (100%) gradient to EtOAc/hexane (40/60) afforded the title intermediate as a red solid 1.20 g (73.2%).

Step H: Preparation of 2,3-ethylenedioxy-6-benzyloxymethyl-9-benzyloxy-12-(2,3,4,5-tetra-O-benzyl-β-D-glucopyranosyl)-6,7,12,13-tetrahydroindolo[2,3-a]pyrrolo[3,4-c]carbazole-5,7-dione (8)

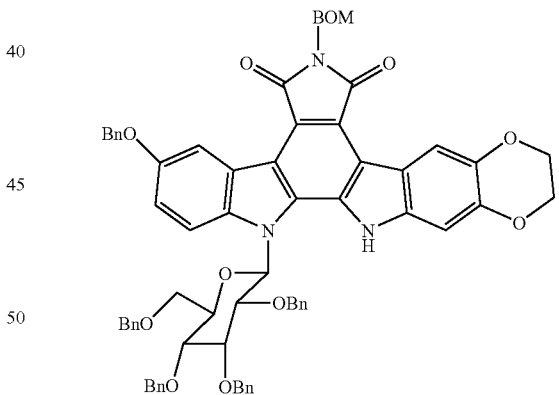

To a solution of 8 (550 mg, 0.485 mmol) in DMF (28 mL) was added palladium(II) trifluoroacetate (338.5 mg, 1.18 mmol), and stirred at 80° C. for one hour. The solution was cooled to room temperature, diluted with EtOAc (280 mL), and washed with HCl (1 M), NaHCO₃, brine (150 mL) and H₂O (3×120 mL). The organic layer was dried over Na₂SO₄, filtered and concentrated. Flash silica gel chromatography eluting with EtOAc/hexane (3:7) afforded 404 mg (73.6%) as a yellow solid.

Step I: Preparation of 2,3-ethylenedioxy-6-hydroxymethyl-9-hydroxy-12-(β-D-glucopyranosyl)-6,7,12,13-tetrahydroindolo[2,3-a]pyrrolo[3,4c]carbazole-5,7-dione (9)

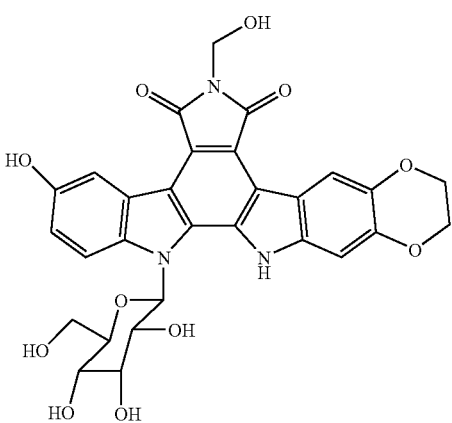

To a solution of 8 (140 mg, 0.1236 mmol) in HOAc (25 mL) was added palladium hydroxide [Pd(OH)₂, 140 mg]. The reaction was shaken under a hydrogen atmosphere (50 psi) at ambient temperature for 63 hours. The mixture was filtered through an Acrodisc syringe filter and concentrated in vacuo to give a crude solid. Flash chromatography eluting with MeOH/HOAc/EtOAc (12/1/87) afforded 42.0 mg (57.5%) as a yellow solid.

Step J: Synthesis of 2,3-ethylenedioxy-9-hydroxy-12-(β-D-glucopyranosyl)-6,7,12,13-tetrahydroindolo[2,3-a]pyrrolo[3,4-c]carbazole-5,7-dione (Ia)

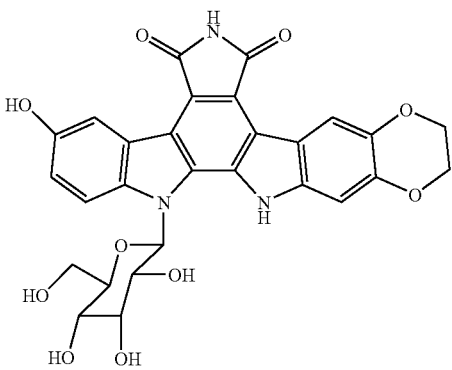

To a solution of 9 (5.0 mg, 0.00845 mmol) in MeOH (0.5 mL) was added NH₄OH (1.5 mL). The mixture was stirred at ambient temperature for 3 hours, then concentrated in vacuo to give a crude solid. Recrystallization with MeOH/hexane/CHCl₃ afforded 4.3 mg (90.5%) as a yellow solid.

EXAMPLE 2

Synthesis of 2,3-methylenedioxy-9-hydroxy-12-(β-D-glucopyranosyl)-6,7,12,13-tetrahydroindolo[2,3-a]pyrrolo[3,4-c]carbazole-5,7-dione (Ib)

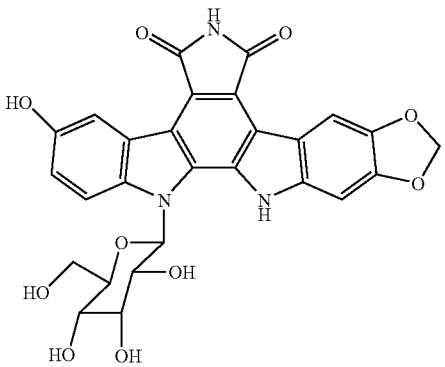

Step A: Preparation of 3,4-methylenedioxytoluene (10)

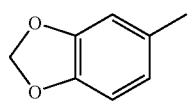

A mixture of 4-methylcatechol (26.0 g, 209.4 mmol) and NaOH (18.4 g, 461.0 mmol) in CH₂Cl₂ (40.0 mL) was heated to 100° C. under nitrogen for 2 hours. The solution was allowed to cool to ambient temperature and diluted with ethyl acetate (500 mL). The mixture was washed with NaHCO₃ (200 mL) and H₂O (2×200 mL). The organic layer was dried over Na₂SO₄, filtered and concentrated to give a crude oil. Flash chromatography eluting with hexane (100%) gradient to ether/hexane (1:1) afforded the title intermediate as a colorless oil 20.5 g (71.9%).

Step B: Preparation of 2-nitro-4, 5-methylenedioxytoluene (11)

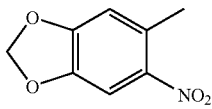

To a solution of 10 (19.0 g, 139.6 mmol) in acetic acid (180 mL) was added a solution of fuming HNO₃ (10 mL) in acetic acid (70 mL) dropwise over 30 minutes. The mixture was stirred at ambient temperature for 10 minutes, then poured into a beaker containing ice to give a crystalline precipitate, which was collected by vacuum filtration and washed with water to afford the crude product. Further purification via recrystallization from CH₂Cl₂/hexane gave the pure product (16.3 g, 64.4%).

Step C: Preparation of (E)-4,5-methylenedioxy-2-nitro-1-pyrrolidinostyrene (12)

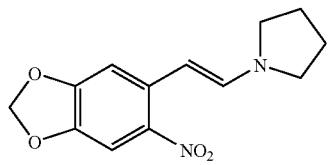

A solution of 11 (15.7 g, 86.74 mmol), N,N-dimethylformamide dimethyl acetal (15.5 g, 130.1 mmol) and pyrrolidine (9.25 g, 130.1 mmol) was heated to 110° C. and stirred for 3 hours under nitrogen. The reaction mixture was cooled, and a mixture of absolute methanol and ethanol (1:1; 250 mL) was added. The product crystallized as a bright red solid. Recovery by suction filtration afforded the product (16.2 g, 71.4%).

Step D: Preparation of 5,6-methylenedioxyindole (13)

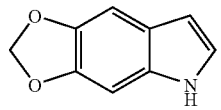

To a solution of 12 (15.7 g, 59.92 mmol) in methanol and THF (200 mL, 1:1) was added Raney nickel (1.5 mL) and hydrazine hydrate (3×2.56 mL, 240 mmol) in three equal portions every half hour at ambient temperature under nitrogen. The solution was then heated at 45° C. for two hours. The mixture was cooled to room temperature and the catalyst was removed by filtration through a bed of Celite, then washed three times with methylene chloride. The filtrate was evaporated and the residue dried by azeotroping with toluene (100 mL) to provide a crude oil. Flash silica gel column chromatography eluting with hexane (100%) gradient to ethyl acetate/hexane (30/70%) afforded the title intermediate as an off-white solid (5.1 g, 52.9%).

Step E: Preparation of 2-(4,5-methylenedioxy-1H-indol-3-yl)-3-[5-benzyloxy-1-(2,3,4,5-tetra-O-benzyl-β-D-glucopyranosyl)-1H-indol-3-yl]-N-benzyloxymethyl maleimide (14)

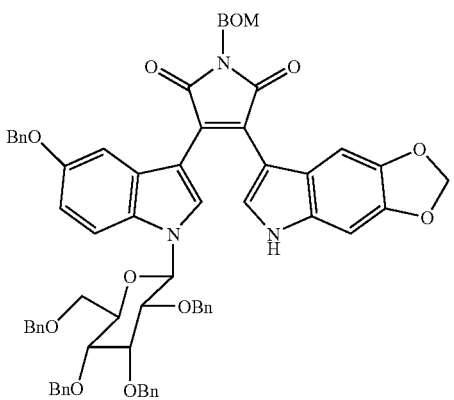

To a solution of 13 (279.0 mg, 1.73 mmol) in THF (35.0 mL) was added lithium hexamethyldisilazide (LiHMDS, 3.46 mL, 3.46 mmol, 1 M in THF) at 0° C. and stirred for 40 minutes. A solution of 6 in THF (20 mL) was added slowly to above mixture, followed by stirring for 20 minutes at 0° C. The mixture was diluted with EtOAc (350 mL), washed with HCl (1 M), NaHCO$_3$, brine, and H$_2$O. The organic layer was dried over Na$_2$SO$_4$, filtered and concentrated to give a crude mixture. Flash silica gel column chromatography eluting with hexane (100%) gradient to ethyl acetate/hexane (40/60%) afforded the title intermediate as a red solid 0.73 g (45.3%).

Step F: Preparation of 2,3-methylenedioxy-6-benzyloxymethyl-9-benzyloxy-12-(2,3,4,5-tetra-O-benzyl-β-D-glucopyranosysl)-6,7,12,13-tetrahydroindolo[2,3-a]pyrrolo[3,4-c]carbazole-5,7-dione (15)

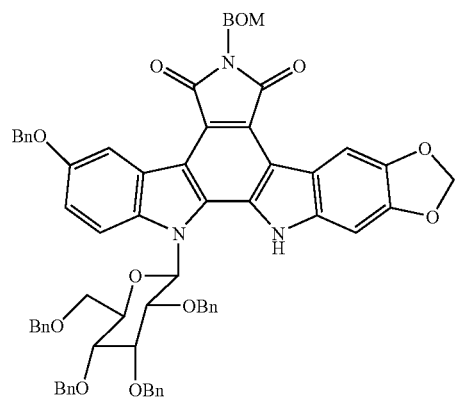

To a solution of 14 (650 mg, 0.58 mmol) in DMF (36 mL) was added palladium(II) trifluoroacetate (405 mg, 1.22 mmol), and the reaction was stirred at 80° C. for one hour. The solution was cooled to room temperature and diluted with EtOAc (350 mL), then washed with HCl (1 M), NaHCO$_3$, brine (150 mL) and H$_2$O (3×150 mL). The organic layer was dried over Na$_2$SO$_4$, filtered and concentrated. Flash silica gel column chromatography eluting with EtOAc/hexane (3:7) afforded 248 mg (38.2%) as a yellow solid.

Step G: Preparation of 2,3-methylenedioxy-6-hydroxymethyl-9-hydroxy-12-(β-D-glucopyranosyl)-6,7,12,13-tetrahydroindolo[2,3-a]pyrrolo[3,4-c]carbazole-5,7-dione (16)

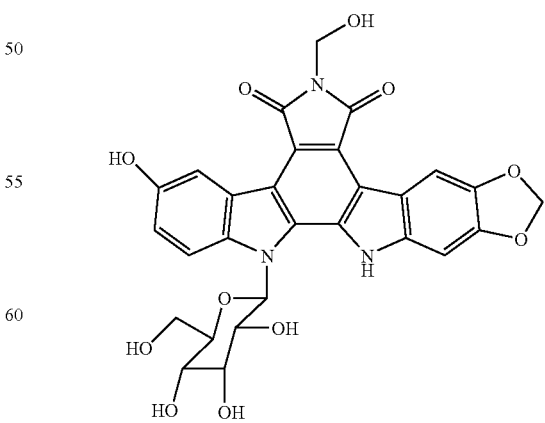

To a solution of 15 (150 mg, 0.1341 mmol) in HOAc (10 mL) was added palladium hydroxide (150 mg). The reaction was shaken under an atmosphere of H$_2$ (50 psi) at ambient temperature for 60 h. The mixture was filtered through an Acrodisc syringe filter and concentrated in vacuo to give a crude solid. Flash silica gel column chromatography eluting with MeOH/AcOH/EtOAc (12/1/87) afforded 56.2 mg (76.7%) as a yellow solid.

Step H. Synthesis of 2,3-methylenedioxy-9-hydroxy-12-(β-D-glucopyranosyl)-6,7,12,13-tetrahydroindolo[2,3-a]pyrrolo[3,4-c]carbazole-5,7-dione (Ib)

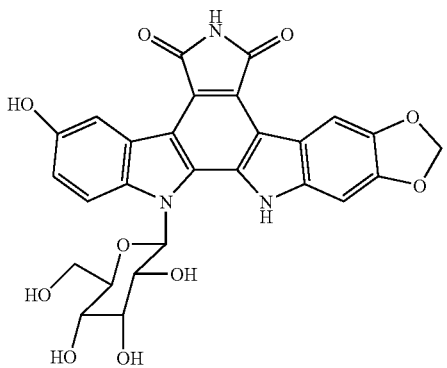

To a solution of 16 (30.0 mg, 0.052 mmol) in MeOH (2.0 mL) was added NH$_4$OH (4.0 mL). The mixture was stirred at ambient temperature for 3 hours, then concentrated in vacuo to give a crude solid. Flash silica gel column chromatography eluting with MeOH/AcOH/EtOAc (12/1/87) afforded 26.1 mg (91.1%) as a yellow solid.

EXAMPLE 3

Synthesis of 2,3-(isopropylenedioxy)-9-hydroxy-13-(β-D-glucopyranosyl)-6,7,12,13-tetrahydroindolo[2,3-a]pyrrolo[3,4-c]carbazole-5,7-dione (Ic)

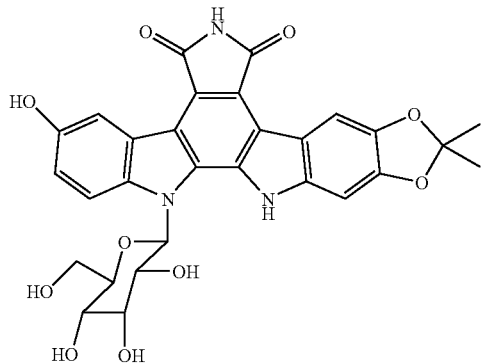

Step A: Preparation of 4-methyl-2',2'-dimethyl-1,3-benzodioxole (17)

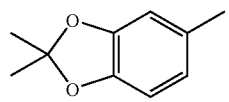

A mixture of 4-methylcatechol (75.0 g, 604.2 mmol, Aldrich), phosphorous pentoxide (85.8 g, 302.3 mmol) in acetone (200 mL) and toluene (200 mL) was refluxed under nitrogen for 50 hours. The solution was allowed to cool to ambient temperature and diluted with ether (500 mL). The mixture was washed with 2 M NaOH (2×200 mL) and H$_2$O (2×200 mL). The organic layer was dried over Na$_2$SO$_4$, filtered and concentrated to give a crude oil. Flash chromatography eluting with hexane (100%) gradient to ether/hexane (1:1) afforded the title intermediate as a colorless oil (82.0 g, 82.7%).

Step B: Preparation of 4-methyl-5-nitro-2',2'-dimethyl-1,3-benzodioxole (18)

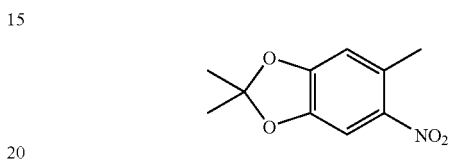

To a solution of 17 (65.0 g, 395.9 mmol) in HOAc (450 mL) was added a solution of fuming HNO$_3$ (35 mL) in acetic acid (100 mL) over 30 minutes. The mixture was stirred at ambient temperature for 10 minutes, then poured into a beaker containing ice to give a crystalline precipitate which was collected by vacuum filtration and washed with water to afford the crude product (77.1 g, 93.8%).

Step C: Preparation of (E)-4,5-(isopropylenedioxy)-2-nitro-1-pyrrolidinostyrene (19)

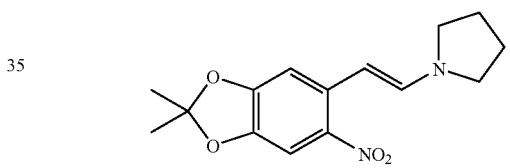

A solution of 18 (45 g, 215.1 mmol), N,N-dimethylformamide dimethyl acetal (38.45 g, 322.7 mmol) and pyrrolidine (22.95 g, 322.7 mmol) were heated to 110° C. and stirred for 16 hours under nitrogen. The reaction mixture was cooled, and a mixture of absolute methanol and ethanol (1:1; 600 mL) was added. The product crystallized as a bright red solid. Recovery by suction filtration afforded the product (51.0 g, 81.5%).

Step D: Preparation of 5,6-(isopropylenedioxy)indole (20)

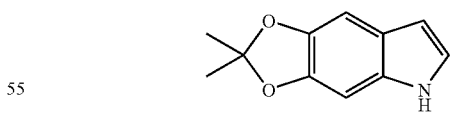

To a solution of 19 (50.0 g, 171.7 mmol) in methanol and THF (400 mL, 1:1) was added Raney nickel (4.0 mL) and hydrazine hydrate (3×7.13 mL, 686.6 mmol) in three equal portions every 30 minutes at ambient temperature under nitrogen. The solution was heated at 45° C. for two hours. The mixture was cooled to room temperature and the catalyst was removed by filtration through a bed of Celite, then washed three times with methylene chloride. The filtrate was evaporated and the residue dried azeotropically with toluene (100 mL) to give a crude oil. Flash silica gel column chromatography eluting with hexane (100%) gradient to ethyl acetate/hexane (30/70%) afforded the title intermediate as an off-white solid, which was futher purified via recrystallization with benzene/petroleum ether (2:8) to give the pure product (15.1 g, 46.2%).

Step E: Preparation of 3-[(4,5-isopropylenedioxy-1H-indol-3-yl)]-4-[5-benzyloxy-1-(2,3,4,5-tetra-O-benzyl-β-D-glucopyranosyl)-1H-indol-3-yl]-N-benzyloxymethyl maleimide (21)

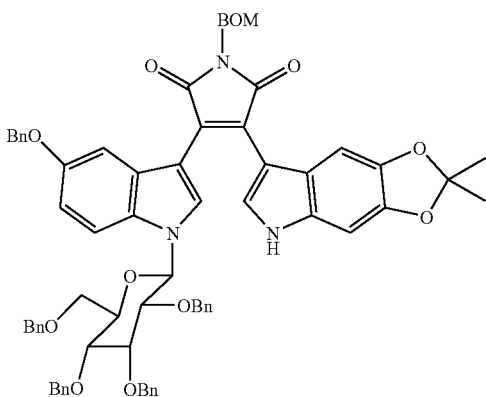

To a solution of 20 (2.27 mg, 12.02 mmol) in THF (150 mL) was added lithium hexamethyldisilazide (LiHMDS, 12.02 mL, 12.02 mmol, 1 M in THF) at 0° C. and the solution was stirred for 40 minutes. A solution of 6 (5.0 g, 4.81 mmol) in THF (50 mL) was added slowly to the above mixture, followed by stirring for 20 minutes at 0° C. The mixture was diluted with EtOAc (400 mL), then washed with HCl (1 M), NaHCO₃, brine, and H₂O. The organic layer was dried over Na₂SO₄, filtered and concentrated to give a crude mixture. Flash silica gel column chromatography eluting with hexane (100%) gradient to ethyl acetate/hexane (40/60%) afforded the title intermediate as a red solid (3.02 g, 54.71%).

Step F: Preparation of 2,3-isopropylenedioxy-6-benzyloxymethyl-9-benzyloxy-12-(2,3,4,5-tetra-O-benzyl-β-D-glucopyranosyl)-6,7,12,13-tetrahydroindolo[2,3-a]pyrrolo[3,4-c]carbazole-5,7-dione (22)

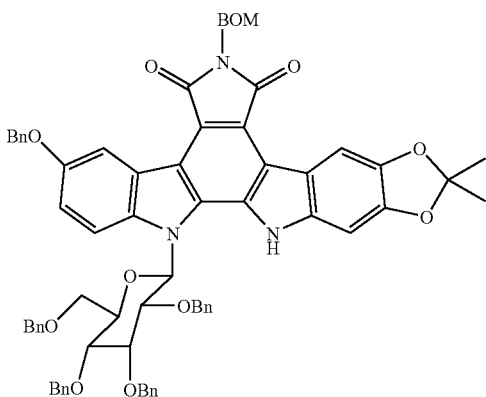

To a solution of 21 (1.60 g, 1.39 mmol) in DMF (85 mL) was added palladium(II) trifluoroacetate (657 mg, 2.93 mmol), and the solution was stirred at 80° C. for two hours. The solution was cooled to room temperature and diluted with EtOAc (250 mL), then washed with HCl (1 M), NaHCO₃, brine (150 mL), and H₂O (3×150 mL). The organic layer was dried over Na₂SO₄, filtered and concentrated. Flash silica gel column chromatography eluting with EtOAc/hexane (3:7) afforded 1.02 g (63.7%) as a yellow solid.

Step G: Preparation of 2,3-isopropylenedioxy-6-hydroxymethyl-9-hydroxy-12-(β-D-glucopyranosyl)-6,7,12,13-tetrahydroindolo[2,3-a]pyrrolo[3,4-c]carbazole-5,7-dione (23)

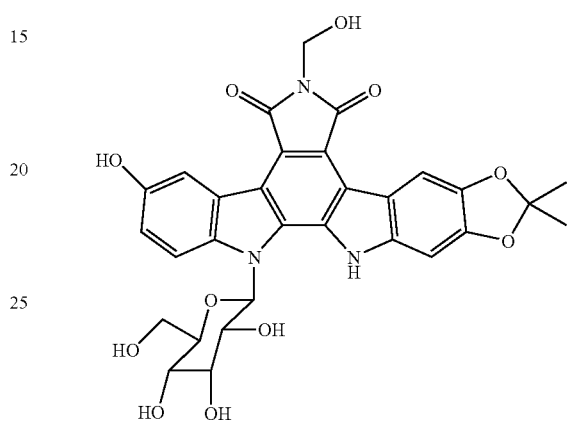

To a solution of 22 (280 mg, 0.244 mmol) in HOAc (12 mL) was added palladium hydroxide (100 mg). The reaction was shaken under an atmosphere of H₂ (50 psi) at ambient temperature for 60 h. The mixture was filtered through an Acrodisc syringe filter and concentrated in vacuo to give a crude solid. Flash silica gel column chromatography eluting with MeOH/AcOH/EtOAc (12/1/87) afforded 135 mg (91.4%) as a yellow solid.

Step H: Synthesis of 2,3-isopropylenedioxy-9-hydroxy-12-(β-D-glucopyranosyl)-6,7,12,13-tetrahydroindolo[2,3-a]pyrrolo[3,4-c]carbazole-5,7-dione (Ic)

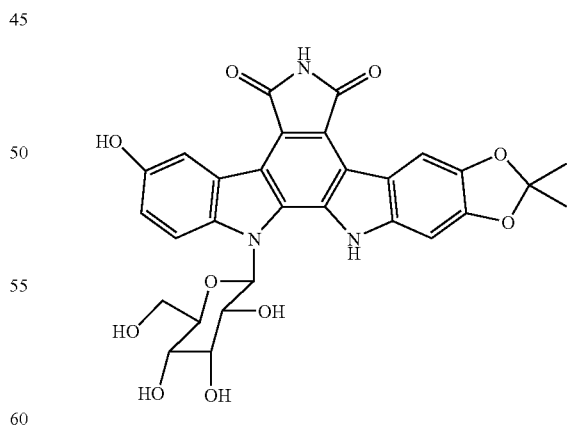

To a solution of 23 (100.0 mg, 0.165 mmol) in MeOH (7.0 mL) was added NH₄OH (6.0 mL). The mixture was stirred at ambient temperature for 2 hours, then concentrated in vacuo to give a crude solid. Flash silica gel column chromatography eluting with MeOH/HOAc/EtOAc (12/1/87) afforded 81.0 mg (85.3%) as a yellow solid.

EXAMPLE 4

Synthesis of 2,3-dimethoxy-9-hydroxy-13-(β-D-glucopyranosyl)-6,7,12,13-tetrahydroindolo[2,3-a]pyrrolo[3,4-c]carbazole-5,7-dione (Id)

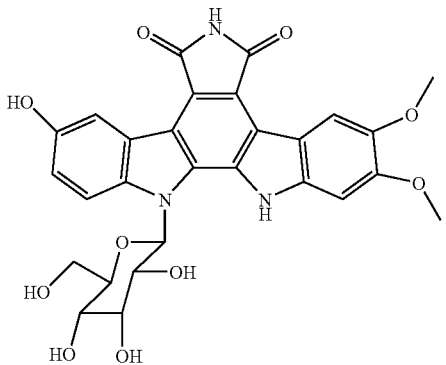

Step A: Preparation of 3-[(4,5-dimethoxy-1H-indol-3-yl)]-4-[5-benzyloxy-1-(2,3,4,5-tetra-O-benzyl-β-D-glucopyranosyl)-1H-indol-3-yl]-N-benzyloxymethyl maleimide (24)

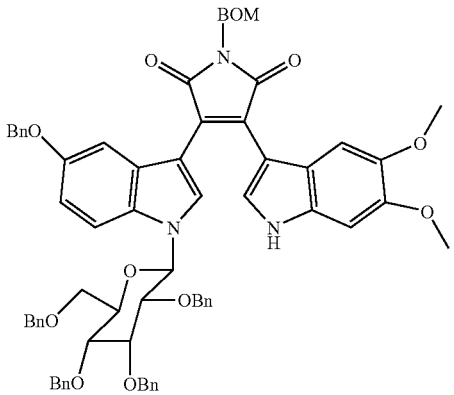

To a solution of 5,6-dimethoxyindole (441 mg, 2.49-mmol) in THF (50 mL) was added lithium hexamethyldisilazide (LiHMDS, 4.98 mL, 4.98 mmol, 1 M in THF) at 0° C. and the solution was stirred for 40 minutes. A solution of 6 (2.25 g, 2.16 mmol) in THF (30 mL) was added slowly to the above mixture, followed by stirring for 20 minutes at 0° C. The mixture was diluted with EtOAc (250 mL), then washed with HCl (1 M), NaHCO₃, brine, and H₂O. The organic layer was dried over Na₂SO₄, filtered and concentrated to give a crude mixture. Flash silica gel column chromatography eluting with hexane (100%) gradient to ethyl acetate/hexane (60/40%) afforded the title intermediate as a red solid (2.79 g, 98.6%).

Step B: Preparation of 2,3-dimethoxy-6-benzyloxymethyl-9-benzyloxy-12-(2,3,4,5-tetra-O-benzyl-β-D-glucopyranosyl)-6,7,12,13-tetrahydroindolo[2,3-a]pyrrolo[3,4-c]carbazole-5,7dione (25)

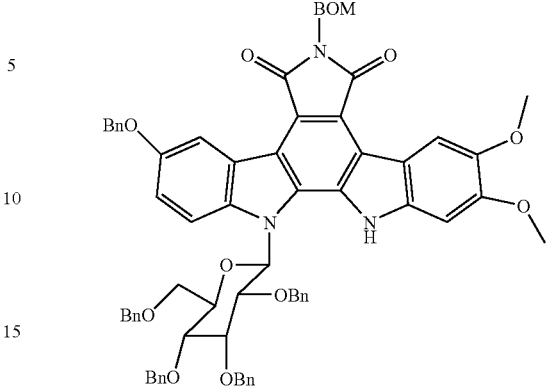

To a solution of 24 (1.50 g, 1.32 mmol) in DMF (60 mL) was added palladium(II) trifluoroacetate (923 mg, 2.77 mmol), and the solution was stirred at 80° C. for two hours. The solution was cooled to room temperature and diluted with EtOAc (250 mL), then washed with HCl (1 M), NaHCO₃, brine (150 mL), and H₂O (3×150 mL). The organic layer was dried over Na₂SO₄, filtered and concentrated. Flash silica gel column chromatography eluting with EtOAc/hexane (3:7) afforded 769 mg (51.4%) as a yellow solid.

Step C: Synthesis of 2,3-isopropylenedioxy-9-hydroxy-12-(β-D-glucopyranosyl)-6,7,12,13-tetrahydroindolo[2,3-a]pyrrolo[3,4-c]carbazole-5,7-dione (Id)

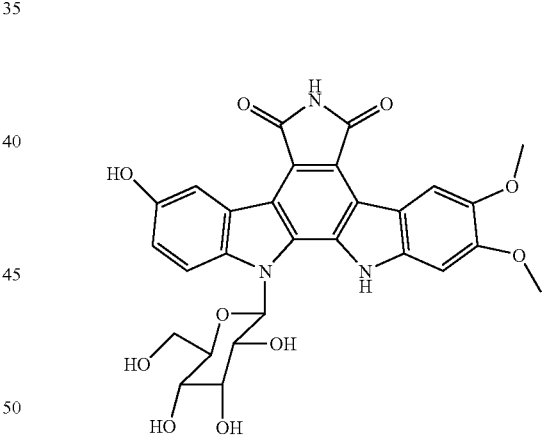

To a solution of 25 (600 mg, 0.529 mmol) in HOAc (25 mL) was added palladium hydroxide (600 mg). The reaction was shaken under an atmosphere of H₂ (50 psi) at ambient temperature for 60 hours in a Parr shaker. The solution was filtered through an Acrodisc syringe filter and concentrated in vacuo to provide a solid. The solid was dissolved in MeOH (150 mL) and aqueous NH₄OH (50 mL). The mixture was stirred at ambient temperature for 1.5 hours, then concentrated in vacuo to provide the crude product. Flash silica gel chromatography eluting with MeOH/HOAc/EtOAc (12/1/87) afforded 166 mg (60.0%) of desired product as a yellow solid.

EXAMPLE 5

Synthesis of 2,3-ethylenedioxy-9-hydroxy-13-(β-D-glucopyranosyl)-6,7,12,13-tetrahydroindolo[2,3-a]pyrrolo[3,4-c]carbazole-5,7-dione (IIa)

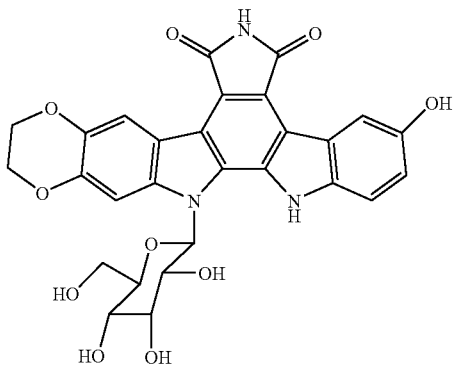

Step A: Preparation of 3-bromo-4-(4,5-ethylenedioxy-1H-indol-3-yl)-N-benzyloxymethylmaleimide (26)

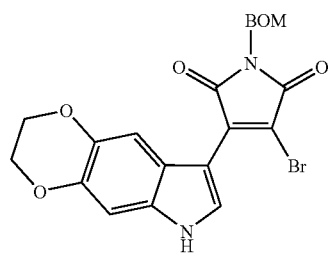

To a solution of 4 (2.1 g, 12.0 mmol) in benzene (100 mL) was added methylmagnesium iodide (4.4 mL, 13.19 mmol, 3 M in ether) at 0° C. After stirring for one hour, a solution of N-benzyloxymethyl-3,4-dibromomaleimide (4.5 g, 12.0 mmol) in benzene (30 mL) and THF (50 mL) was added slowly. The reaction mixture was stirred at 0° C. for 30 minutes and then warmed to room temperature for one hour. The mixture was diluted with EtOAc (250 mL), then washed with HCL (100 mL, 0.3 M), NaHCO₃ (100 mL) and H₂O (100 mL). The organic layer was dried over Na₂SO₄, filtered and concentrated. Flash silica gel chromatography, eluting with a hexane gradient to EtOAc/hexane (3:2) afforded the title intermediate as a yellow solid (2.83 g, 50.5%).

Step B: Preparation of 3-bromo-4-[4,5-ethylenedioxy-1-(2,3,4,5-tetra-O-benzyl-β-D-glucopyranosyl)-1H-indol-3-yl]-N-benzyloxymethylmaleimide (27)

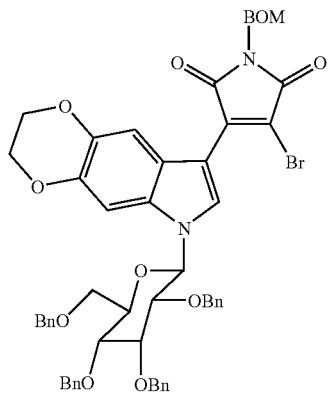

To a solution of 26 (2.7 g, 5.75 mmol), 2,3,4,5-tetra-O-benzyl-D-glucopyranose (9.33 g, 17.26 mmol) and triphenylphosphine (4.53 g, 17.26 mmol) in THF (150 mL) at −78° C. was added diisopropylazodicarboxylate (DIAD) (3.4 mL, 17.26 mmol) dropwise. Stirring was continued at −78° C. for 3 hours, then the solution was warmed to 0° C. with the aid of a ice-water bath and stirring continued for 2 hours. The mixture was diluted with EtOAc (300 mL), then washed with HCL, brine and H₂O. The organic layer was dried over Na₂SO₄, filtered and concentrated. Flash silica gel chromatography, eluting with a toluene gradient to toluene/EtOAc (25:1) afforded the title intermediate as a yellow solid 3.15 g (55.3%).

Step C: Preparation of 3-(5-benzyloxy-1H-indol-3-yl)-4-[4,5-ethylenedioxy-1-(2,3,4,5-tetra-O-benzyl-β-D-glucoyranosyl)-1H-indol-3-yl]-N-benzyloxymethylmaleimide (28)

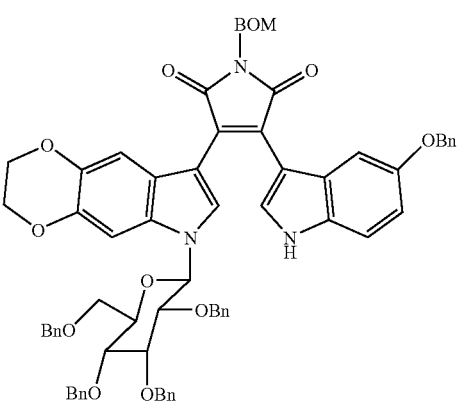

To a solution of 5-benzyloxyindole (1.52 g, 6.8 mmol) in THF (70.0 mL) was added lithium hexamethyldisilazide (LiHMDS, 6.8 mL, 6.8 mmol, 1 M in THF) at 0° C., and the solution stirred for 30 minutes. A solution of 27 in THF (80 mL) was added slowly to the above mixture, followed by stirring for 30 minutes at 0° C. The mixture was diluted with EtOAc (300 mL), then washed with HCl (1 M), NaHCO₃, brine, and H₂O. The organic layer was dried over Na₂SO₄, filtered and concentrated to give the crude product. Flash silica gel chromatography eluting with a hexane (100%) gradient to EtOAc/hexane (2:3) afforded the title intermediate as a red solid 1.62 g (52.6%).

Step D: Preparation of 2,3-ethylenedioxy-6-benzyloxymethyl-9-benzyloxy-13-(2,3,4,5-tetra-O-benzyl-β-D-glucopyranosyl)-6,7,12,13-tetrahydroindolo[2,3-a]pyrrolo[3,4-c]carbazole-5,7-dione (29)

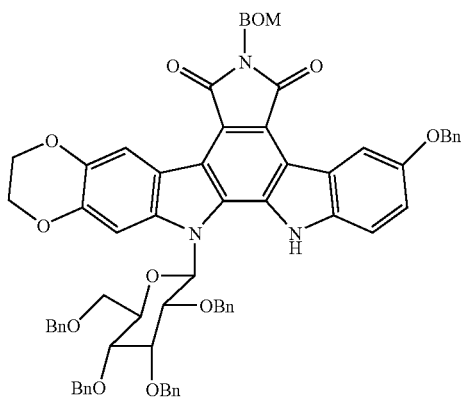

To a solution of 28 (1.0 g, 0.882 mmol) in DMF (50 mL) was added palladium(II) trifluoroacetate (615.4 mg, 1.85 mmol), and the solution was stirred at 80° C. for 1 hour. The solution was cooled to room temperature and diluted with EtOAc (350 mL), then washed with HCl (1 M), NaHCO₃, brine (150 mL) and H₂O (3×150 mL). The organic layer was dried over Na₂SO₄, filtered and concentrated. Flash silica gel chromatography eluting with EtOAc/hexane (3:7) afforded 471.0 g (47.2%) of desired product as a yellow solid.

Step E: Synthesis of 2,3-ethylenedioxy-9-hydroxy-13-(β-D-glucopyranosyl)-6,7,12,13-tetrahydroindolo[2,3-a]pyrrolo[3,4-c]carbazole-5,7-dione (IIa)

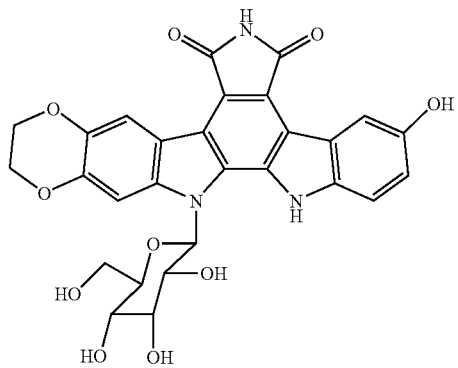

To a solution of 29 (350 mg, 0.309 mmol) in HOAc (12 mL) was added palladium hydroxide (350 mg). The reaction was shaken under an atmosphere of H₂ (50 psi) at ambient temperature for 62 hours in a Parr shaker. The solution was filtered through an Acrodisc syringe filter and concentrated in vacuo to provide a solid. The solid was dissolved in MeOH (200 mL) and aqueous NH₄OH (10 mL). The mixture was stirred at ambient temperature for 3 hours, then concentrated in vacuo to provide the crude product. Flash silica gel chromatography eluting with MeOH/HOAc/EtOAc (12/1/87) afforded 164 mg (94.5%) of desired product as a yellow solid.

EXAMPLE 6

Synthesis of 2,3-methylenedioxy-9-hydroxy-13-(β-D-glucopyranosyl)-6,7,12,13-tetrahydroindolo[2,3-a]pyrrolo[3,4-c]carbazole-5,7-dione (IIb)

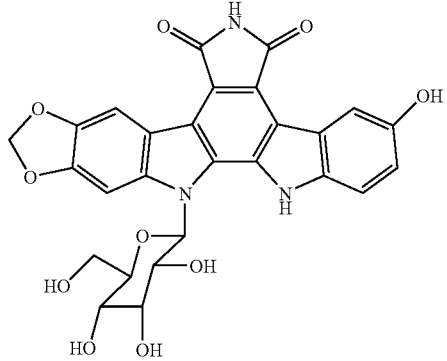

Step A: Preparation of 3-bromo-4-(5,6-methylenedioxy-1H-indol-3-yl)-N-benzyloxymethylmaleimide (30)

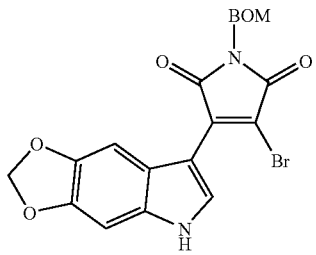

To a solution of 13 (2.7 g, 16.75 mmol) in benzene (100 mL) was added methylmagnesium iodide (6.14 mL, 18.42 mmol, 3 M in ether) at 0° C. The solution was stirred for 1 hour, and then a solution of N-benzyloxymethyl-3,4-dibromomaleimide (6.28 g, 16.75 mmol) in benzene (30 mL) and THF (50 mL) was added slowly. The reaction mixture was stirred at 0° C. for 30 minutes, then warmed to room temperature and stirred for 1 hour. The mixture was diluted with EtOAc (200 mL), then washed with HCL (100 mL, 0.3 M), NaHCO₃ (100 mL) and H₂O (100 mL). The organic layer was dried over Na₂SO₄, filtered and concentrated. Crystallization of the crude oil with MeOH afforded the title intermediate as a yellow solid (2.92 g, 38.2%).

Step B: Preparation of 3-bromo-4-[5,6-methylenedioxy-1-(2,3,4,5-tetra-O-benzyl-β-D-glucopyranosyl)-1H-indol-3-yl]-N-benzyloxymethylmaleimide (31)

47

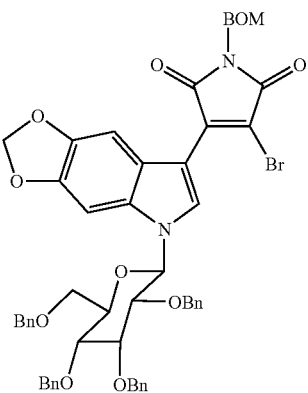

To a solution of 30 (2.3 g, 5.05 mmol), 2,3,4,5-tetra-O-benzyl-D-glucopyranose (8.2 g, 15.2 mmol) and triphenylphosphine (4.0 g, 15.2 mmol) in THF (150 mL) at −78° C. was added diisopropylazodicarboxylate (DIAD) (2.98 mL, 15.2 mmol) dropwise. The solution was stirred at −78° C. for 3 hours, then warmed to 0° C. and stirred further for 2 hours. The mixture was diluted with EtOAc (300 mL), then washed with HCl, brine, and H₂O. The organic layer was dried over Na₂SO₄, filtered and concentrated. Flash silica gel chromatography eluting with a toluene gradient to toluene/EtOAc (25:1) afforded the title intermediate as a yellow solid 3.05 g (61.8%).

Step C: Preparation of 3-(5-benzyloxy-1H-indol-3-yl)-4-[5,6-methylenedioxy-1-(2,3,4,5tetra-O-benzyl-β-D-glucopyranosyl)-1H-indol-3-yl]-N-benzyloxymethylmaleimide (32)

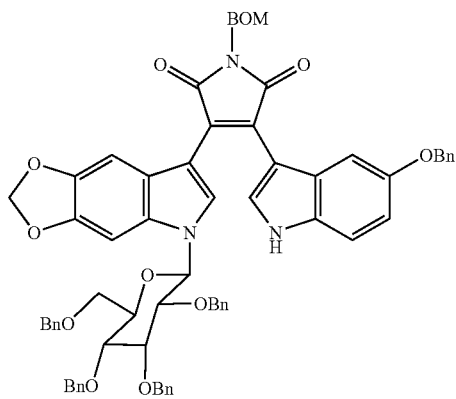

To a solution of 5-benzyloxyindole (822.0 mg, 3.68 mmol) in THF (35 mL) was added lithium hexamethyldisilazide (LiHMDS, 3.68 mL, 3.68 mrol, 1 M in THF) at 0° C., and the resulting solution was stirred for 40 minutes. A solution of 31 in THF (20 mL) was added slowly to the above mixture, followed by stirring for 20 minutes at 0° C. The mixture was diluted with EtOAc (300 mL), then washed with HCl (1 M), NaHCO₃, brine, and H₂O. The organic layer was dried over Na₂SO₄, filtered and concentrated to provide the crude product. Flash silica gel chromatography eluting with a hexane (100%) gradient to EtOAc/hexane (2:3) afforded the title intermediate as a red solid (1.56 g, 91.2%).

48

Step D: Preparation of 2,3-methylenedioxy-6-benzyloxymethyl-9-benzyloxy-13-(2,3,4,5-tetra-O-benzyl-β-D-glucopyranosyl)-6,7,12,13-tetrahydroindolo[2,3-a]pyrrolo[3,4-c]carbazole-5,7-dione (33)

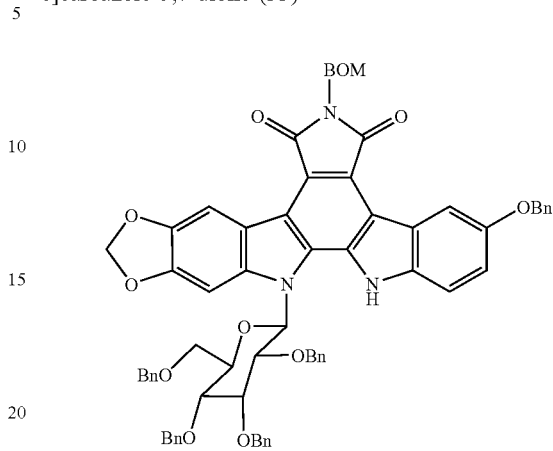

To a solution of 32 (1.45 g, 1.294 mmol) in DMF (75 mL) was added palladium(II) trifluoroacetate (904 mg, 2.72 mmol), and the solution was stirred at 80° C. for 1 hour. The solution was cooled to room temperature and diluted with EtOAc (350 mL), then wash with HCl (1 M), NaHCO₃, brine, and H₂O (3×150 mL). The organic layer was dried over Na₂SO₄, filtered and concentrated. Flash silica gel chromatography eluting with EtOAc/hexane (3:7) afforded 1.05 g (72.6%) of the desired product as a yellow solid.

Step E: Synthesis of 2,3-methylenedioxy-9-hydroxy-13-(β-D-glucopyranosyl)-6,7,12,13-tetrahydroindolo[2,3-a]pyrrolo[3,4-c]carbazole-5,7-dione (IIb)

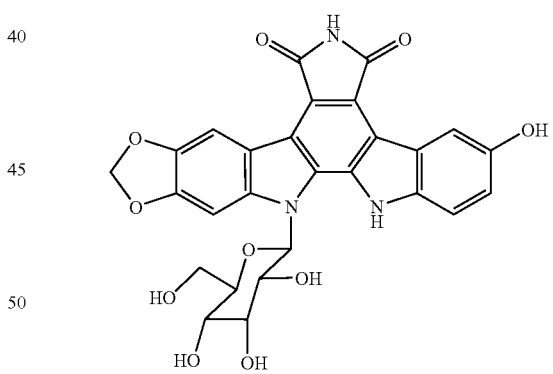

To a solution of 33 (300 mg, 0.268 mmol) in HOAc (14 mL) was added palladium hydroxide (300 mg). The reaction was shaken under an atmosphere of H₂ (50 psi) at ambient temperature for 60 hours in a Parr shaker. The solution was filtered through an Acrodisc syringe filter and concentrated in vacuo to provide the crude product as a solid. The solid was dissolved in MeOH (20.0 mL) and aqueous NH₄OH (30.0 mL), stirred at ambient temperature for 2 hours, and then concentrated in vacuo to provide the crude product. Flash silica gel chromatography eluting with MeOH/HOAc/EtOAc (12/1/87) afforded 92.0 mg (62.7%) as a yellow solid.

EXAMPLE 7

Typical Experimental Procedure for the Synthesis Compounds with the Following General Formula

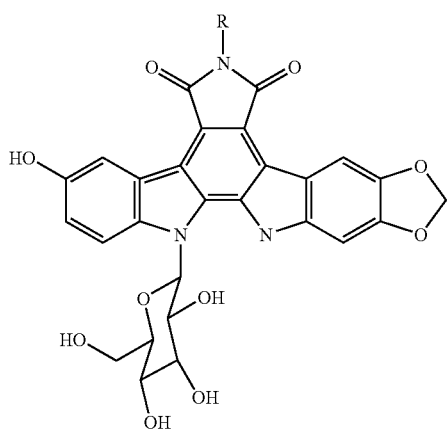

To a solution of the anhydride YPX-2-21 (32 mg, 0.05834 mmol) in DMF (1.8 mL) was added appropriate hydrazide or amine [0.5834 mmol] (see Table 1). The reaction was placed under atmosphere of nitrogen at 95° C. for 2 h. The mixture was diluted with water (12 mL) and stirred at 0° C. for two h. The precipitate was filtered and washed with water and ethyl ether to obtain the product (see Table 1 for yields).

TABLE 1

Modofication at the Imide Ring

| S. No. | R | Yield % |
|---|---|---|
| 1 | —NH₂ | 72 |
| 2 | [structure] | 27.4 |
| 3 | [structure] | 68 |
| 4 | [structure] | 76 |
| 5 | [structure] | 87.2 |
| 6 | [structure] | 90.2 |
| 7 | [structure] | 66.4 |
| 8 | [structure] | 27.4 |
| 9 | [structure] | 52 |
| 10 | [structure] | 84 |
| 11 | [structure] | 100 |
| 12 | [structure] | 69.4 |
| 13 | [structure] | 70.4 |
| 14 | [structure] | 54 |
| 15 | [structure] | 67.6 |
| 16 | —CHO | 76 |

EXAMPLE 8

Biological Evaluation a.) Topoisomerase I assay. Reaction buffer (10.3 μL H₂O, 2.0 μL 10×buffer, 1.5 μL 100 μM MgCl₂, and 3.2 μL 500 mM KCl) was prepared and kept on ice. 10×Buffer was prepared by mixing 2 mL 2M Tris pH 7.5, 15.3 μL 10% DTT, 100 μL 0.5 M EDTA, 75 μL 20 mg/mL BSA, and 7.935 μL H₂O. Test poisons were prepared in DMSO at such concentrations that the final incubation mixture was 5% DMSO. DNA mix was prepared by dissolving 55 mL of pHOT1 DNA solution (0.25 μg/μL) with 715 μL reaction buffer. Topo I mix was prepared by mixing 14 μL of Topo I solution (2 units/μL) with 266 μL of reaction buffer. Proteinase K solution was prepared fresh as 10 mg/mL in 1% SDS. Gel loading buffer was prepared by dissolving 1 mg bromophenol blue in 100 μL H₂O, then adding 900 μL 50% glycerol. Topotecan (Camptosar) and 3,9-dihydroxy-12-(β-D-glucopyranosyl)-6,7,12,13-tetrahydroindolo[2,3-a]pyrrolo[3,4-c]carbazole-5,7-dione (ALS-007) were used as positive controls.

The assay was conducted as follows. DNA mix (14 μL) was added to sample tubes containing 1 μL of test poison solution and stored on ice. Next, 5 μL of Topo I mix was added, the solution was mixed with the pipettor, then incubated with gentle rocking in a 37° C. water bath for 30 minutes. The reactions were stopped via addition of 2 μL of proteinase K solution, and incubation was continued for another 30 minutes, then placed on ice. 2.2 μL of 5 M NaCl and 75 μL of EtOH were added to the tubes, the tubes were vortexed briefly, then placed on dry ice for 1 hour. The DNA was pelleted by centrifugation at 16,000×g for 10 minutes at 4° C. EtOH was removed from each tube using a gel loading pipette tip, and the DNA pellet was resuspended in 18 μL of reaction buffer and 2 μL of gel loading buffer. The samples were vortexed briefly, then spun for 15 seconds in a microcentrifuge to force all the liquid to the bottom of the tubes. The samples were loaded onto a 1% agarose gel made with 1×TBE containing 2 μg/mL chloroquine. The gels were run at 35 V for 15 hours in 1×TBE. Gels were stained with 0.5 μg/mL ethidium bromide in 1×TBE for 1 hour, then destained for 30 minutes in $H_2O$. Gels were photographed with a digital camera, and the digitized images analyzed using NIH software. $IC_{50}$ values were determined by comparing supercoiled DNA band density (negative controls containing 5 μL reaction buffer in place of Topo I mix) with the supercoiled DNA bands remaining in the test samples.

TABLE 2

Poisoning of Human Topoisomerase I by Indolocarbazole Analogues

| Agent | $IC_{50}$ (μM) |
|---|---|
| Topotecan | 31.3 |
| ALS-007 | 20.9 |
| 9 | 3.9 |
| 16 | 3.6 |
| Ia | 5.4 |
| Ib | 3.6 |
| 23 | 130 |
| Ic | 8.1 |
| IIa | >400 |
| IIb | >400 | b.) In vitro Cytotoxicity Assay. 96-Well tissue culture cluster plates were seeded with 100 μL of cell suspension (5×10³ cells/mL), and incubated overnight for cell anchorage and acclimation. Cells were propagated under sterile conditions in RPMI 1640 or DMEM with 10% fetal bovine serum, 2 mM L-glutamine, and sodium bicarbonate (complete medium), and incubated at 37° C. The test compounds were prepared in DMSO and then diluted in complete media. A range of eight concentrations was used for each test drug to establish cytotoxicity, with eight replicates for each concentration. All dosing was conducted using a Biomek 2000 robotic liquid handler. The plates were incubated at 37° C. with 5% $CO_2$ and 95% relative humidity. The data were analyzed for cytotoxicity using the MTS assay 3–5 days (depending upon the growth rate of the cell lines) after commencement of treatment. MTS (3-(4,5-dimethylthiazol-2-yl)-5-(3-carboxymethoxyphenyl)-2-(4-sulfophenyl)-2H-tetrazolium is bio-reduced by viable cells into a soluble formazan that absorbs at 490 nm, allowing simple spectrophotometric measurement of viable cells. Topotecan (Camptosar) and 3,9-dihydroxy-12-(β-D-glucopyranosyl)-6,7,12,13-tetrahydroindolo[2,3-a]pyrrolo[3,4-c]carbazole-5,7-dione (ALS-007) were used as positive controls.

c.) MTS Assay. A solution of 40 μL of MTS/PES solution (purchased from Promega Corporation) was added to each well, and incubated for one to four hours. The absorbance of formazan in each monolayer was measured at 490 nm on a Coulter microplate reader. The data were processed in a spreadsheet program to provide a dose-response curve, allowing determination of the $IC_{50}$.

TABLE 3

Growth-Inhibitory Activity Against Various Human Tumor Cell Lines

| | $IC_{50}$ (μM) | | |
|---|---|---|---|
| Agent | HT-29 Colon | DU-145 Prostate | OVCAR-3 Ovarian |
| Topotecan | 0.533 | 0.030 | <0.003 |
| ALS-007 | 9.96 | 0.338 | <0.01 |
| 9 | >10 | 0.718 | <0.01 |
| 16 | >10 | 0.549 | <0.01 |
| Ia | >10 | 0.845 | <0.01 |
| Ib | >10 | 0.460 | <0.01 |
| 23 | >10 | 3.52 | 0.043 |
| Ic | >10 | 2.36 | 0.036 |

As illustrated by the results in Table 2, in a side-by-side comparison, the compounds disclosed in this invention provide a stronger poisoning effect against human Topo I than the control compounds, topotecan (a clinically-used Topo I poison/antitumor agent) and ALS-007, an experimental indolocarbazole previously disclosed[11]. Additionally, in a side-by-side comparison, the compounds disclosed in this invention exhibit in vitro cytotoxicity profiles against a series of three human tumor cell lines similar to the two control compounds (Table 3).

CITATIONS

1. Liu, L. F. *Ann. Rev. Biochem.* 1989, 58, 351–375.
2. Schneider, E.; Hsiang, Y-H; Liu, L. F. *Adv. Pharmacol.* 1990, 21, 149–183.
3. Champoux, J. J. *Adv. Pharmacol.* 1994, 29A, 71–82.
4. Redinbo, M. R.; Stewart, L.; Kuhn, P.; Champoux, J. J.; Hol, W. G. J. *Science* 1998, 279, 1504–1513.
5. Pommier, Y.; Tanizawa, A.; Kohn, K. W. *Adv. Pharmacol.* 1994, 29B, 73–92.
6. Giovanella, B. P.; Stehlin, J. S.; Wall, M. E.; Wani, M.; Nicholas, A. W.; Liu, L. F.; Silber, R.; Potmesil, M. *Science* 1989, 246, 1046–1048.
7. Lima, C. D. Wang, J. C.; Mondragon, A. *Nature* 1994, 367, 138–146.
8. Husain, I.; Mohler, J. L.; Seigler, H. F.; Besterman, J. M. *Cancer Res.* 1994, 54, 539–546.
9. Kojiri, K.; Kondo, H.; Arakawa, H.; Ohkubo, M.; Suda, H. U.S. Pat. No. 5,591,842 Jan. 7, 1997.
10. Kojiri, K.; Kondo, H.; Arakawa, H.; Ohkubo, M.; Suda, H. U.S. Pat. No. 5,922,860 Jul. 13, 1999.
11. Kojiri, K.; Kondo, H.; Arakawa, H.; Ohkubo, M.; Suda, H. U.S. Pat. No. 5,668,271 Sep. 16, 1997.
12. Kojiri, K.; Kondo, H.; Arakawa, H.; Ohkubo, M.; Suda, H. U.S. Pat. No. 5,804,564 Sep. 8, 1998.
13. Arakawa, H.; Iguchi, T.; Yoshinari, K.; Kojiri, K.; Suda, H.; Okura, A. *Jpn. J Cancer Res.* 1993, 84, 574–581.
14. Arakawa, H.; Tomoko, I.; Masashi, M.; Yoshinari, T.; Katsuhisa, K.; Hiroyuki, S.; Okura, A.; Nishimura, S. *Cancer Res.* 1995, 55, 1316–1320.
15. Yoshinari, T.; Ohkubo, M.; Fukasawa, K.; Egashira, S.; Hara, Y.; Matsumoto, M.; Nakai, K.; Arakawa, H.; Morishima, H.; Nishimura, S. *Cancer Res.* 1999, 59, 4271–4275.

16. Zembower, D. E.; Zhang, H.; Lineswala, J. P.; Kuffel, M. J.; Aytes, S. A.; Ames, M. M. *Bioorg. Med. Chem. Lett.* 1999, 9, 145–150.
17. Batcho, A. D.; Leimgruber, W. *Org. Synth. Coll.* Vol. VII 1990, 34–41.
18. Kaneko, T.; Wong, H.; Okamoto, K. T.; Clardy, J. *Tetrahedron Lett.* 1985, 26, 4015–4018.
19. Ohkubo, M.; Nishimura, T.; Jona, H.; Honma, T.; Ito, S.; Morishima, H. *Tetrahedron* 1997, 53, 5937–5950.
20. Blair, J. B.; Kurrasch-Orbaugh, D.; Marona-Lewicka, D.; Cumbay, M. G.; Watts, V. J.; Barker, E. L.; Nichols, D. E. *J. Med. Chem.* 2000, 43, 4701–4710.

We claim:
1. A compound of formula I or formula II:

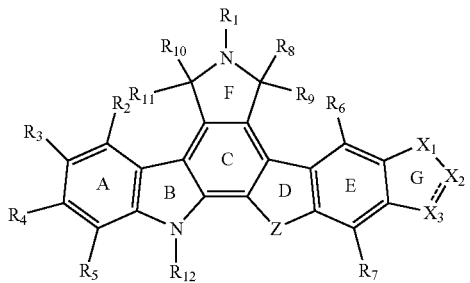

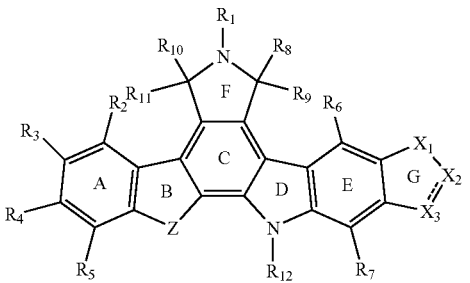

wherein in each compound $R_1$ is selected from the group consisting of H, OH, $NH_2$, $NO_2$, $SO_2NRR'$, COR, $CO_2R$ and CONRR', alkylcarbonyl, alkylcarbonyloxy, $C_{1-6}$ alkyl, $C_{1-6}$ alkyloxy, $C_{1-6}$ alkylamino, di($C_{1-6}$ alkyl)amino, $C_{1-6}$ alkylamino-$C_{1-6}$ alkyl, di($C_{1-6}$ alkyl)amino-$C_{1-6}$ alkyl, or cyclo($C_{3-6}$) alkyl, $C_{1-6}$ alkylsulphinyl, $C_{1-6}$ alkylsulphonyl, wherein said alkyl is straight-chained or branched, saturated or unsaturated, and is optionally substituted with one or more substituents selected from the group consisting of halogen $N_3$, CN, $NO_2$, SR, OR, NRR', SOR, $SO_2R$, $SO_3R$, $SO_2NRR'$, COR, $CO_2R$ and CONRR', or aryl, aryl-$C_{1-6}$ alkyl, aryloxy, aryl-$C_{1-6}$ alkyloxy, arylcarbonyloxy, arylamino, di(aryl)amino, aryl-$C_{1-6}$ alkylamino, di(aryl-$C_{1-6}$ alkyl)amino, arylsulphinyl, arylsulphonyl, wherein said alkyl is defined as above; aryl comprises six membered aromatic carbocycles or polycyclic aromatic rings and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or heterocycle, (heterocycle)$C_{1-6}$ alkyl, (heterocycle)oxy, (heterocycle)$C_{1-6}$ alkyloxy, (heterocycle)carbonyloxy, (heterocycle)amino, di(heterocycle)amino, [(heterocycle)$C_{1-6}$ alkyl]amino, di[(heterocycle)$C_{1-6}$ alkyl]amino, wherein said alkyl is defined as above; heterocycle comprises 3–8 membered heterocycles or polycyclic systems and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbocycle, (carbocycle)$C_{1-6}$ alkyl, (carbocycle)oxy, (carbocycle)$C_{1-6}$ alkyloxy, (carbocycle)carbonyloxy, (carbocycle)amino, di(carbocycle)amino, [(carbocycle)$C_{1-6}$ alkyl]amino, di[(carbocycle)$C_{1-6}$ alkyl]amino, wherein said alkyl is defined as above; carbocycle comprises 3–8 membered carbocycles or polycyclic systems and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbamate of the formula —NH—CO—R", wherein R" comprises H, $C_{1-6}$ alkyl, aryl-$C_{1-6}$ alkyl, heterocycle-$C_{1-6}$ alkyl, wherein said alkyl, aryl and heterocycle are defined as above, or aryl carbamate of the formula —NH—CO—Ar, wherein said aryl is defined as above, or heterocycle carbamate of the formula —NH—CO-heterocycle, wherein said heterocycle is defined as above, or carbocycle carbamate of the formula —NH—CO-carbocycle, wherein said carbocycle is defined as above, or sulfonamide of the formula —NH—S(O)$_n$R, wherein said n is 1 or 2, $R_2$, $R_3$, $R_4$, $R_5$, $R_6$ and $R_7$ are independently selected from the group consisting of H, halogen, CN, OH, SH, $NH_2$, $N_3$, $NO_2$, $CO_2R$, CONRR', $SO_3R$, $SO_2NRR'$, alkylcarbonyloxy, alkylcarbamate, $C_{1-6}$ alkyl, $C_{1-6}$ alkoxy, $C_{1-6}$ alkylsulphinyl, $C_{1-6}$ alkylsulphonyl, $C_{1-6}$ alkylamino, di($C_{1-6}$ alkyl)amino, $C_{1-6}$ alkylamino-$C_{1-6}$ alkyl, di($C_{1-6}$ alkyl)amino-$C_{1-6}$ alkyl, or cyclo($C_{3-6}$)alkyl, wherein said alkyl is straight-chained or branched, saturated or unsaturated, and is optionally substituted with one or more substituents selected from the group consisting of halogen, $N_3$, CN, $NO_2$, SR, OR, NRR', SOR, $SO_2R$, $SO_3R$, $SO_2NRR'$, COR, $CO_2R$ and CONRR', or aryl, aryl-$C_{1-6}$ alkyl, aryloxy, aryl-$C_{1-6}$ alkyloxy, arylsulphinyl, arylsulphonyl, aryl-$C_{1-6}$ alkylsulphinyl, aryl-$C_{1-6}$ alkylsulphonyl, arylcarbonyloxy, arylcarbamate, arylamino, di(aryl)amino, aryl-$C_{1-6}$ alkylamino, di(aryl-$C_{1-6}$ alkyl)amino, wherein said alkyl is defined as above; aryl comprises six membered aromatic carbocycles or polycyclic aromatic rings and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or heterocycle, (heterocycle)$C_{1-6}$ alkyl, (heterocycle)oxy, (heterocycle)$C_{1-6}$ alkyloxy, (heterocycle)sulphinyl, (heterocycle)sulphonyl, (heterocycle)$C_{1-6}$ alkylsulphinyl, (heterocycle)$C_{1-6}$ alkylsulphonyl, (heterocycle)carbonyloxy, (heterocycle)amino, di(heterocycle)amino, [(heterocycle)$C_{1-6}$ alkyl]amino, di[(heterocycle)$C_{1-6}$ alkyl]amino, wherein said alkyl is defined as above; heterocycle comprises 3–8 membered heterocycles or polycyclic systems and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbocycle, (carbocycle)$C_{1-6}$ alkyl, (carbocycle)oxy, (carbocycle)$C_{1-6}$ alkyloxy, (carbocycle)carbonyloxy, (carbocycle)amino, di(carbocycle)amino, [(carbocycle)$C_{1-6}$ alkyl]amino, di[(carbocycle)$C_{1-6}$ alkyl]amino, wherein said alkyl is defined as above; carbocycle comprises 3–8 membered carbocycles or polycyclic systems and is optionally substituted with one or more substituents selected from the group consisting of halogen, R, $N_3$, CN, $NO_2$, SR, OR, NRR', SOR, $SO_2R$, $SO_3R$, $SO_2NRR$, COR, $CO_2R$ and CONRR', or $R_2$ and $R_3$, $R_4$ and $R_5$, or $R_3$ and $R_4$ together form a non-aromatic 5–8 membered cyclic or heterocyclic rings;

$R_8$, $R_9$, $R_{10}$ and $R_{11}$ are independently selected from the group consisting of H, OH, $NH_2$, alkylcarbonyloxy, alkylcarbamate, $C_{1-6}$ alkyl, $C_{1-6}$ alkyloxy, $C_{1-6}$ alkylamino, di($C_{1-6}$ alkyl)amino, $C_{1-6}$ alkylamino-$C_{1-6}$ alkyl, di($C_{1-6}$ alkyl)amino-$C_{1-6}$ alkyl, cyclo($C_{3-6}$)alkyl, aryl, carbocyclic or heterocyclic, wherein said alkyl, aryl, carbocyclic and heterocyclic are defined above; or $R_8$ and $R_9$ together, $R_{10}$ and $R_{11}$ together can independently form =O;

$R_{12}$ represents an optionally substituted pentose or hexose group, or said pentose and/or hexose may be linked to form an oligosaccharide or H, OH, $NH_2$, $SO_2NRR'$, $CO_2H$, CONRR', $C_{1-12}$ alkylcarbonyl, $C_{1-12}$ alkyloxycarbonyl, $C_{1-12}$ alkylcarbonyloxy, $C_{1-12}$ alkyl, $C_{1-12}$ epoxyalkyl, $C_{1-12}$ alkyloxy, $C_{1-6}$ alkyloxy-$C_{1-6}$ alkyl, $C_{1-6}$ alkylthio-$C_{1-6}$ alkyl, $C_{1-12}$ alkylamino, di($C_{1-12}$ alkyl)amino, $C_{1-6}$ alkylamino-$C_{1-6}$ alkyl, di($C_{1-6}$ alkyl)amino-$C_{1-6}$ alkyl, $C_{1-6}$ alkyloxy-$C_{1-6}$ alkylamino, di($C_{1-6}$ alkyloxy-$C_{1-6}$ alkyl)amino, $C_{1-6}$ alkylamino-$C_{1-6}$ alkyloxy, di($C_{1-6}$ alkylamino)-$C_{1-6}$ alkyloxy, cyclo($C_{3-6}$ alkyl, $C_{1-12}$ alkylsulphinyl, $C_{1-12}$ alkylsulphonyl, $C_{1-6}$ alkylsulphinyl-$C_{1-6}$ alkyl, $C_{1-6}$ alkylsulphonyl-$C_{1-6}$ alkyl, polyethyleneglycole (PEG), polyamine, wherein said alkyl is straight-chained or branched, saturated or unsaturated, and is optionally substituted with one or more substituents selected from the group consisting of halogen, $N_3$, CN, $NO_2$, SR, OR, NRR', SOR, $SO_2R$, $SO_3R$, $SO_2NRR'$, COR, $CO_2R$ and CONRR', or aryl, aryl-$C_{1-6}$ alkyl, aryloxy, aryl-$C_{1-6}$ alkyloxy, arylcarbonyloxy, arylamino, di(aryl)amino, aryl-$C_{1-6}$ alkylamino, di(aryl-$C_{1-6}$ alkyl)amino, arylsulphinyl, aryl-$C_{1-6}$ sulphonyl, arylsulphinyl-$C_{1-6}$ alkyl, arylsulphonyl-$C_{1-6}$ alkyl, wherein said alkyl is defined as above; aryl comprises six membered aromatic carbocycles or polycyclic aromatic rings and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or heterocycle, (heterocycle)$C_{1-6}$ alkyl, (heterocycle)oxy, (heterocycle)$C_{1-6}$ alkyloxy, (heterocycle)carbonyloxy, (heterocycle)amino, di(heterocycle)amino, [(heterocycle)$C_{1-6}$ alkyl]amino, di[(heterocycle)$C_{1-6}$ alkyl]amino, wherein said alkyl is defined as above; heterocycle comprises 3–8 membered heterocycles or polycyclic systems and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbocycle, (carbocycle)$C_{1-6}$ alkyl, (carbocycle)oxy, (carbocycle)$C_{1-6}$ alkyloxy, (carbocycle)carbonyloxy, (carbocycle)amino, di(carbocycle)amino, [(carbocycle)$C_{1-6}$ alkyl]amino, di[(carbocycle)$C_{1-6}$ alkyl]amino, wherein said alkyl is defined as above; carbocycle comprises 3–8 membered carbocycles or polycyclic systems and is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', or carbamate of the formula —NH—CO—R", wherein R" comprises H, $C_{1-6}$ alkyl, aryl-$C_{1-6}$ alkyl, heterocycle-$C_{1-6}$ alkyl, wherein said alkyl, aryl and heterocycle are defined as above, or aryl carbamate of the formula —NH—CO—Ar, wherein said aryl is defined as above, or heterocycle carbamate of the formula —NH—CO-heterocycle, wherein said heterocycle is defined as above, or carbocycle carbamate of the formula —NH—CO-carbocycle, wherein said carbocycle is defined as above, or sulfonamide of the formula —NH—S(O)$_n$R, wherein said n is 1 or 2, $X_1$, $X_2$ and $X_3$ are independently selected from the group consisting of O, N, S, NH, (CH)$_n$, (CH$_2$)$_n$, CO, wherein said n is 1, 2 or 3, and the hydrogen atom in NH, CH, $CH_2$ is optionally substituted with one or more substituents selected from the group consisting of halogen, R, $N_3$, CN, $NO_2$, SR, OR, NRR', SOR, $SO_2R$, $SO_3R$, $SO_2NRR'$, COR, $CO_2R$ and CONRR', Z is selected from the group consisting of $CH_2$, NH, O, S;

R and R' are independently selected from the group consisting of H, $C_{1-12}$ alkyl, aryl, heterocyclic, carbocyclic, and cyclo($C_{3-6}$)alkyl, wherein said alkyl is optionally substituted with one or more substituents selected from the group consisting of halogen, OH, $NH_2$, $N_3$, SR, CN, $CO_2H$, $CO_2(C_{1-3}$ alkyl), S($C_{1-3}$ alkyl), O($C_{1-3}$ alkyl), NH($C_{1-3}$ alkyl), NH($C_{1-3}$ alkyl)$_2$, and is saturated or unsaturated; or R and R' together with the nitrogen atom to which they are attached form a non-aromatic 5–8 membered heterocycle containing one or two of the same or different heteroatoms selected from the group consisting of O, N, and S; or a pharmaceutically acceptable salt thereof;

with the proviso that when $R_2=R_4=R_5=R_6=R_7=H$, $R_8$ and $R_9$ together is =O, $R_{10}$ and $R_{11}$ together is =O, $X_1=X_3=O$, $X_2=(CH_2)_{1-3}$, $R_3$ is any of H, OH, $NH_2$, $C_{1-6}$ alkyl, aryl-$C_{1-6}$ alkyl, or mono- or polyfluorinated $C_{1-6}$ alkyl, $C_{1-6}$ alkoxy, $C_{1-6}$ alkylamino, di($C_{1-6}$ alkyl)amino, $C_{1-6}$ alkylamino-$C_{1-6}$ alkyl, di($C_{1-6}$ alkyl)amino-$C_{1-6}$ alkyl, cyclo($C_{3-6}$)alkyl, aryl or heterocycle, and Z=NH, $R_{12}$ is not unsubstituted or unmodified β-D-glucopyranosyl.

2. A compound according to claim 1 wherein Z is NH.

3. A compound according to claim 1 wherein $R_2$, $R_3$, $R_4$, and $R_5$ are independently selected from —H, —OH, $C_1$–$C_6$-alkyl, —$N_3$, —$NO_2$, —$NH_2$, and halogen.

4. A compound according to claim 1 wherein $R_2$, $R_3$ and $R_4$ are each H and $R_5$ is OH or F.

5. A compound according to claim 1 wherein $R_2$, $R_3$ and $R_5$, are each H, and $R_4$ is OH, $NH_2$, Br, or F.

6. A compound according to claim 1 wherein $R_2$, $R_4$, and $R_5$ are each H, and $R_3$ is $CH_3$, $N_3$, $NO_2$, $NH_2$, Br, or F.

7. A compound according to claim 1 wherein $R_{12}$ is selected from the group consisting of:

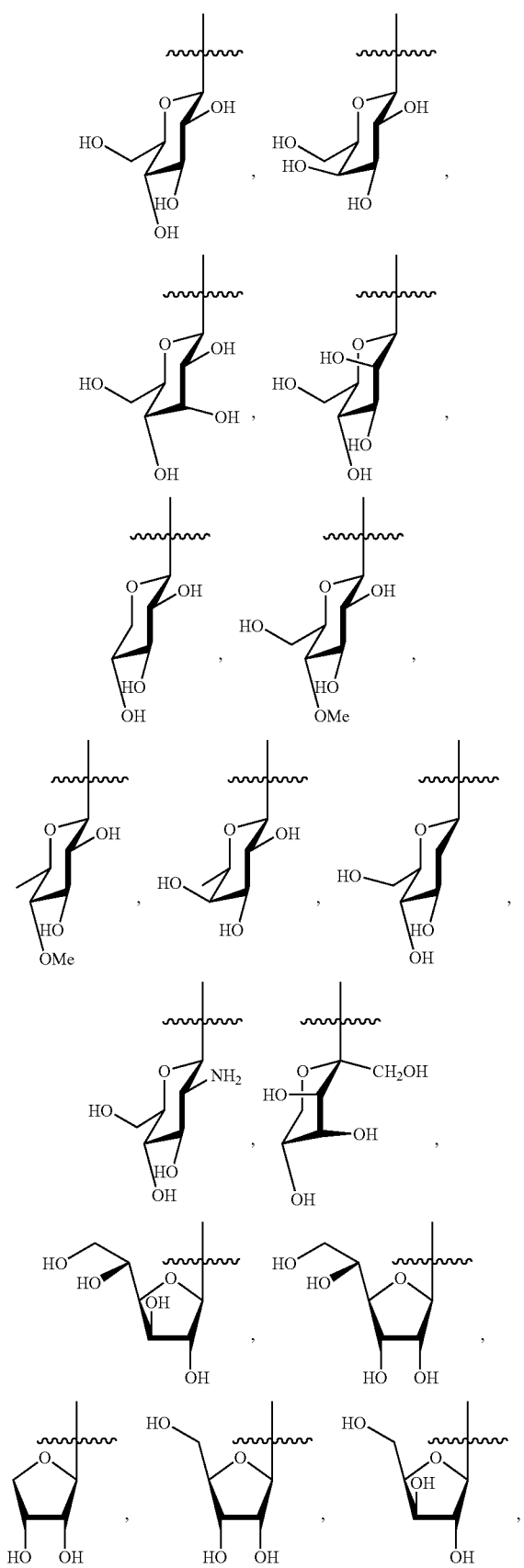

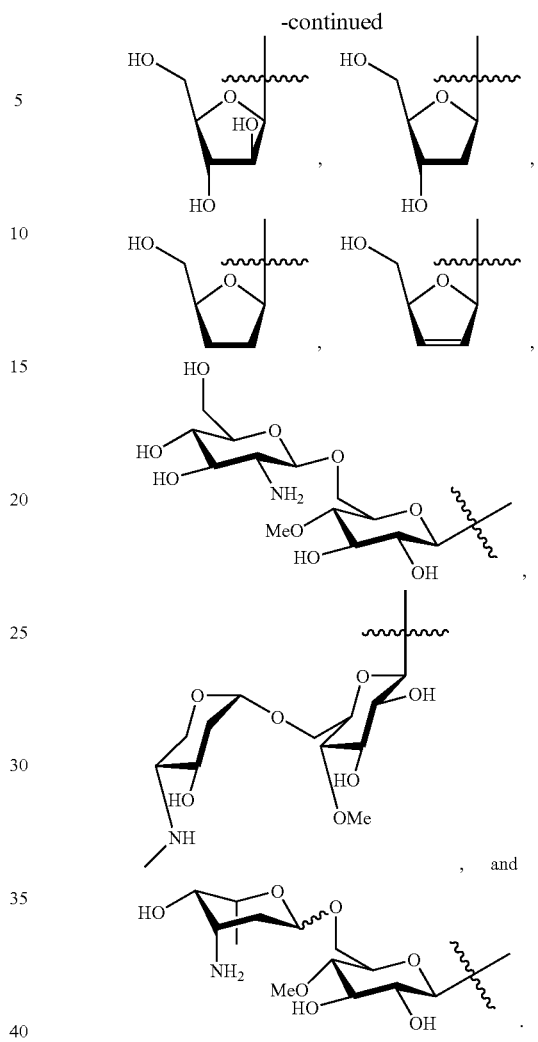

8. A compound according to claim 1 wherein $R_8$ and $R_9$ together and $R_{10}$ and $R_{11}$ together form =O.

9. A compound according to claim 1 wherein $R_1$ is H, $NH_2$, NHCHO, $NHCH(CH_2OH)_2$, or $CH_2CH_2N(CH_2CH_3)_2$.

10. A compound according to claim 1 wherein $X_1$ and $X_3$ are both O and $X_2$ is $(CH_2)_n$, wherein n=1, 2, or 3.

11. A compound according to claim 1 wherein the pentoses and hexoses are optionally substituted by independently replacing one or more hydrogen and/or hydroxy groups of the pentose and hexose with a substituent selected from the group consisting of H, halogen, R, $N_3$, CN, $NO_2$, SR, OR, NRR', SOR, $SO_2R$, $SO_3R$, $SO_2NRR'$, COR, $CO_2R$, CONRR', alkylcarbonyloxy, alkylcarbamate, $C_{1-6}$ alkyl, $C_{1-6}$ alkoxy, $C_{1-6}$ alkylsulphinyl, $C_{1-6}$ alkylsulphonyl, $C_{1-6}$ alkylamino, di($C_{1-6}$ alkyl)amino, $C_{1-6}$ alkylamino-$C_{1-6}$ alkyl, di($C_{1-6}$ alkyl)amino-$C_{1-6}$ alkyl, cyclo($C_{3-6}$)alkyl, aryl, carbocyclic, and heterocyclic, wherein said alkyl, aryl, carbocyclic and heterocyclic groups are as defined in claim 1.

12. A compound according to any one of claims 1 or 11 wherein the pentoses and hexoses are optionally substituted by derivatizing or oxidizing one or more hydroxyl groups of the pentose and hexose.

13. A compound according to any one of claims 1 or 11 wherein the pentoses and hexoses are optionally substituted by replacing one or more ring atoms with a substituent selected from the group consisting of $CH_2$, CHR, $CR_2$, O, S, NH, or NR wherein R and $R_2$ are as defined in claim 1.

14. A compound according to claim 12 wherein the pentoses and hexoses are optionally substituted by replacing one or more ring atoms with a substituent selected from the group consisting of $CH_2$, CHR, $CR_2$, O, S, NH, or NR wherein R and $R_2$ are as defined in claim 1.

15. A method of inhibiting topoisomerase I activity comprising administering to a mammal in need of inhibition of topoisomerase I activity an effective amount of at least one compound of claim 1.

16. A composition for inhibiting topoisomerase I activity comprising an effective amount of at least one compound of claim 1 in combination with a carrier, a pharmaceutical adjuvant, or additive material.

* * * * *